(12) United States Patent
Thorsteinsson et al.

(10) Patent No.: US 7,985,193 B2
(45) Date of Patent: *Jul. 26, 2011

(54) INTELLIGENT ORTHOSIS

(75) Inventors: Freygardur Thorsteinsson, Reykjavik (IS); Helgi Jónsson, Reykjavik (IS); Jose L. Pons, Madrid (ES); Juan C. Moreno Sastoque, Madrid (ES); Fernando J. Brunetti Fernández, Madrid (ES); Antonio M. Cullel Mirada, Valencia (ES); José María Baydal Bertomeu, Bétera (ES); Ricard Barberà Guillem, Xirivella (ES); Mario Comín Clavijo, Bétera (ES); Lambertus Wilhelmus Freriks, Borne (NL); M. Ijzerman, Enschede (NL); Anand V. Nene, Hengelo (NL)

(73) Assignee: Ossur HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 12/402,909

(22) Filed: Mar. 12, 2009

(65) Prior Publication Data

US 2009/0171469 A1 Jul. 2, 2009

Related U.S. Application Data

(63) Continuation of application No. 11/819,534, filed on Jun. 28, 2007, now Pat. No. 7,578,799.

(60) Provisional application No. 60/817,347, filed on Jun. 30, 2006.

(51) Int. Cl.
*A61F 5/00* (2006.01)

(52) U.S. Cl. ............................................ 602/16; 602/32

(58) Field of Classification Search ................ 602/5, 16, 602/19, 32; 128/869; 482/51, 66
See application file for complete search history.

(56) References Cited

U.S. PATENT DOCUMENTS

| 3,358,678 A | 12/1967 | Kultsar |
| 3,969,773 A | 7/1976 | Menschik |

(Continued)

FOREIGN PATENT DOCUMENTS

ES 2251278 4/2006

(Continued)

OTHER PUBLICATIONS

Sumira Rajagopalan, "Firm Strives to Give Amputees Prosthesis with Motor-Driven Kenn Uses a Microprocessor and Sensors to Sin", The Washington Post, Apr. 12, 2004, AB.

(Continued)

*Primary Examiner* — Michael A. Brown
(74) *Attorney, Agent, or Firm* — Bacon & Thomas, PLLC

(57) ABSTRACT

An orthotic frame has proximal and distal frame members joined by a knee joint, and a foot support joined by an ankle joint to a distal end of the distal frame. A knee actuator connected between the proximal and distal frame members has a selective stiffness allowing selection of a relatively rigid stiffness during stance and a relatively flexible stiffness during swing. The stiffness of the knee actuator is selected according to the gait cycle, either mechanically according to dorsal flexion of the ankle joint or electronically according to gait cycle phases recognized based on read sensor data. An ambulatory unit gathers data from sensors located on the orthotic frame. Sensor data may be provided to a base unit for diagnostic and biomechanical evaluation, or evaluated by the ambulatory unit to control active components of the orthotic frame according to the recognized gait cycle phases for functional compensation.

20 Claims, 13 Drawing Sheets

U.S. PATENT DOCUMENTS

| | | | |
|---|---|---|---|
| 4,628,916 A | | 12/1986 | Lerman et al. |
| 4,711,242 A | | 12/1987 | Petrofsky |
| 4,821,707 A | | 4/1989 | Audette |
| 4,872,665 A | * | 10/1989 | Chareire ............... 482/51 |
| 5,038,763 A | | 8/1991 | Wiggins |
| 5,133,773 A | | 7/1992 | Sawamura et al. |
| 5,144,943 A | | 9/1992 | Luttrell et al. |
| 5,252,102 A | | 10/1993 | Singer et al. |
| 5,282,460 A | | 2/1994 | Boldt |
| 5,395,304 A | | 3/1995 | Tarr et al. |
| 5,472,412 A | | 12/1995 | Knoth |
| 5,476,441 A | * | 12/1995 | Durfee et al. ............ 602/23 |
| 5,547,464 A | | 8/1996 | Luttrell et al. |
| 5,658,242 A | * | 8/1997 | McKay et al. ........... 602/16 |
| 5,662,693 A | * | 9/1997 | Johnson et al. .......... 607/49 |
| 5,683,353 A | | 11/1997 | Hamersly |
| 5,728,172 A | | 3/1998 | Krieger |
| 5,772,619 A | | 6/1998 | Corbett |
| 5,888,212 A | | 3/1999 | Petrofsky et al. |
| 5,954,678 A | | 9/1999 | Cruz |
| 5,961,541 A | | 10/1999 | Ferrati |
| 6,080,123 A | | 6/2000 | Pansiera |
| 6,113,642 A | | 9/2000 | Petrofsky et al. |
| 6,117,097 A | | 9/2000 | Ruiz |
| 6,171,272 B1 | | 1/2001 | Akita et al. |
| 6,174,294 B1 | | 1/2001 | Crabb et al. |
| 6,379,393 B1 | | 4/2002 | Mavroidis et al. |
| 6,471,664 B1 | | 10/2002 | Campbell et al. |
| 6,500,138 B1 | | 12/2002 | Irby et al. |
| 6,517,503 B1 | | 2/2003 | Naft et al. |
| 6,834,752 B2 | | 12/2004 | Irby et al. |
| 7,578,799 B2 | * | 8/2009 | Thorsteinsson et al. ......... 602/5 |
| 2002/0094919 A1 | | 7/2002 | Rennex et al. |
| 2002/0183673 A1 | | 12/2002 | Naft et al. |
| 2002/0188238 A1 | | 12/2002 | Townsend et al. |
| 2003/0009308 A1 | | 1/2003 | Kirtley |
| 2003/0062241 A1 | | 4/2003 | Irby et al. |
| 2003/0093021 A1 | | 5/2003 | Goffer |
| 2003/0115031 A1 | | 6/2003 | Dariush et al. |
| 2003/0144620 A1 | | 7/2003 | Sieller et al. |
| 2003/0212356 A1 | | 11/2003 | Scorvo |
| 2004/0049290 A1 | | 3/2004 | Bedard |
| 2004/0049291 A1 | | 3/2004 | Deharde et al. |
| 2004/0054423 A1 | | 3/2004 | Martin |
| 2004/0064195 A1 | | 4/2004 | Herr |
| 2005/0070834 A1 | | 3/2005 | Herr et al. |

FOREIGN PATENT DOCUMENTS

| WO | WO2005/032437 | 4/2005 |
|---|---|---|

OTHER PUBLICATIONS

Joaquin A. Blaya and Hugh Herr, "Adaptive Control of a Variable-Impedance Ankle-Foot Orthosis to Assist Drop-Foot Gain", IEEE Transaction, vol. 12, No. 1 Mar. 2004.

"Clinician's Corner", Foot Maxx.

<http://www.gla.ac.uk/ibls/fab/images/anatomy/gaitcyc2.gif> Apr. 5, 2006.

<http://www.gla.ac.uk/ibls/fab/images/anatomy/dorsdiag.gif> Mar. 9, 2006.

"The Gait Cycle" pp. 712-714.

\* cited by examiner

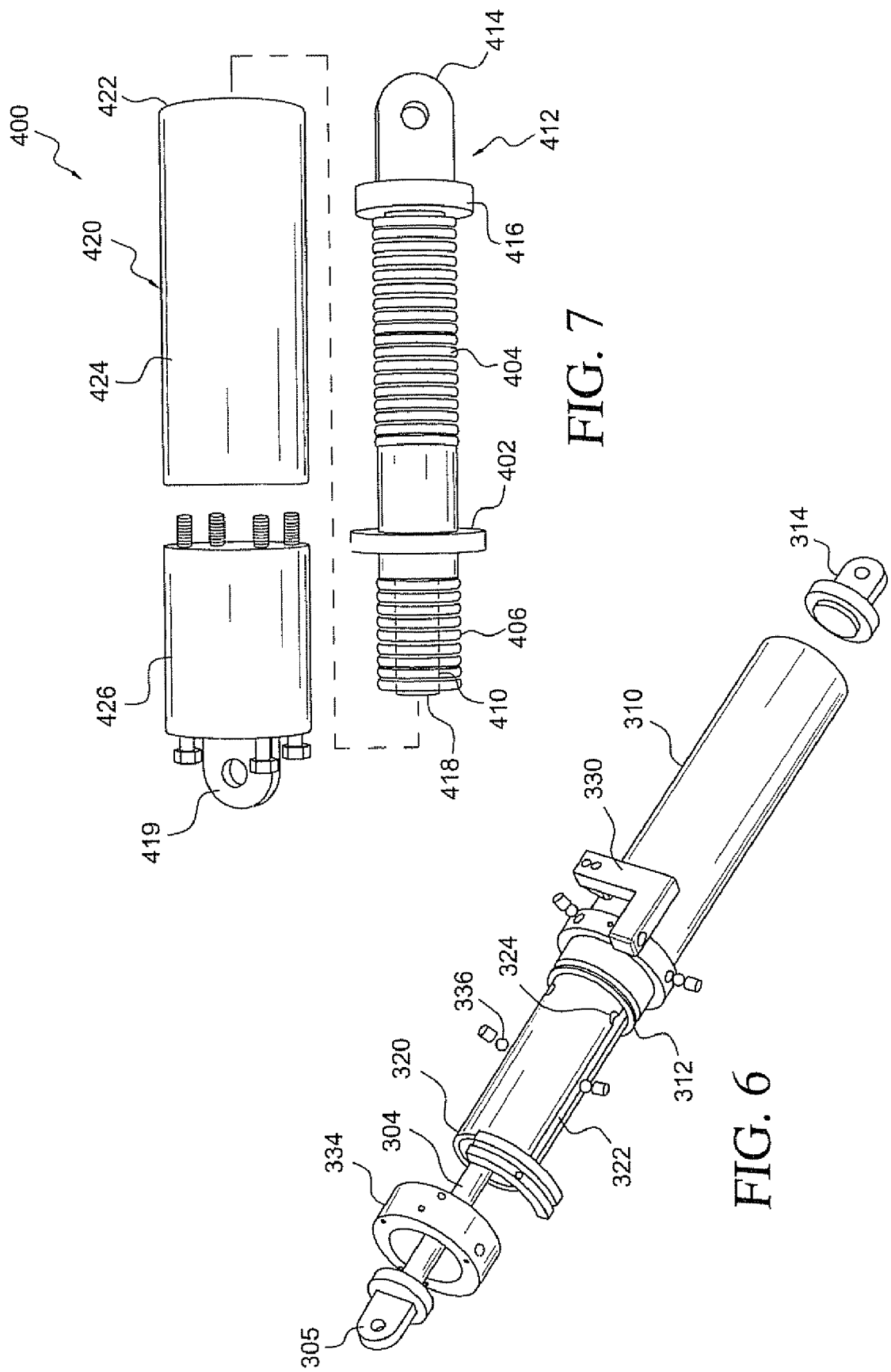

INTELLIGENT ORTHOSIS

CROSS REFERENCE TO RELATED APPLICATION DATA

This application is a continuation of U.S. application Ser. No. 11/819,534 filed Jun. 28, 2007 now U.S. Pat. No. 7,578,799 which claims the benefit of U.S. Provisional Application No. 60/817,347 filed Jun. 30, 2006.

FIELD OF THE INVENTION

The present invention relates an orthotic brace, and more particularly to an intelligent knee, ankle, and foot orthosis for biomechanical evaluation and functional compensation of joint disorders.

BACKGROUND

Patients with partial or complete paralysis or muscular weakness of the extremities often are assisted in mobility by the use of an orthotic device or orthosis. For example, a patient with weakness of leg muscles may employ an orthosis to provide assistance in supporting body weight during the stance phase of the gait cycle.

A knee, ankle, and foot orthosis (KAFO) typically extends from the patient's upper leg to the lower leg, and provides a foot support. In order to accommodate normal flexion of the patient's knee, a knee joint or hinge joins an upper portion of the KAFO (which is worn attached to the patient's upper leg) to a lower portion of the KAFO (which is worn attached to the patient's lower leg). Additionally, an ankle joint may be provided between the lower portion and the foot support to allow, or control, flexion of the foot.

One common aspect of a knee orthotic, including a KAFO, is the ability to lock the knee joint or, hinge in a straight legged position so that the rigidly locked KAFO supports the patient in stance in compensation for weakness or paralysis of the leg muscles.

Various devices have been devised for locking the knee hinge or joint of an orthosis such as a KAFO. However, while it is advantageous to lock the knee for support during stance, it is problematic for the knee to remain locked during the swing phase of the gait cycle.

With an orthotic knee continuously locked, a patient must perform an unnatural and inefficient motion to affect a walking gait, by lifting the leg with the orthosis to provide for clearance of the foot from the ground as the leg swings forward.

Further, in the case of a KAFO, it is more likely that the patient wearing the KAFO suffers from a weakness or abnormality in muscles related to dorsal or plantar flexion of the foot. A patient who has, for example, weakened dorsal flexors of the foot may lack the ability for proper dorsal flexion of the foot during the gait cycle, in addition to lacking leg strength for support. As a result, gait problems resulting from a rigidly locked orthotic knee may be exacerbated by an inability of the patient to dorsally flex the foot and thereby raise the toes to avoid toe drag during the swing phase of the gait.

In addition to the leg lift required for clearance in the leg with a locked knee, further lifting may be required for clearance of the toes or forefoot. Not only does a her awkwardness or inefficiency of the gait result, a safety consideration arises in the increased risk of fall due to toe drag if sufficient clearance is not consistently achieved.

It is therefore desirable for an orthotic knee joint to be selectively lockable, so that support may be provided during the stance phase while knee flexion is allowed during the swing phase to facilitate a more normal, and more efficient, gait. Further, in the case of a KAFO, it is desirable for ankle and knee compensation strategies to be coordinated in function so that the patient's gait is additionally improved.

In addition to gait problems that result from a continuously locked knee, a knee that is rigidly locked does not provide shock absorption that may be achieved by even a small degree of flexion of the knee.

SUMMARY

The present invention relates to an intelligent knee, ankle, and foot orthosis (KAFO). The KAFO incorporates both passive and active components in an orthotic frame to compensate for muscle weakness during walking, standing, and other activities, to support a user and to assist the user in approximating or achieving a normal gait.

The KAFO acts simultaneously on knee and ankle joints to apply active compensation strategies to provide an integral solution to mobility problems related to weakness of leg muscles, and particularly quadriceps weakness.

The KAFO may provide various compensation strategies, including assistance in supporting the patient during loading of the leg (during the stance phase), free or controlled flexion of the knee joint during the swing phase, assistance in push off prior to the swing phase, control of ankle flexion to avoid toe drag or drop foot, and assistance in extension of the knee at the end of the swing phase.

The KAFO comprises a mechanical orthotic frame that has a proximal (thigh) frame portion joined by a knee joint to a distal (shank) frame portion. A foot support is joined to the distal frame portion by an ankle joint.

A patient wears the orthotic frame with the proximal frame portion fitted to a leg above the knee and the distal frame portion fitted to the leg below the knee, and with the knee joint aligned with the patient's knee. The patient's foot is supported on the foot support, and the ankle joint is aligned with the patient's ankle.

A knee actuator is provided to control flexion of the knee joint. In certain embodiments, the knee actuator is a passive or semi-passive device that provides a fixed, selectable, or variable resistance to the flexion of the knee joint. Such a knee actuator restricts the flexion of the knee joint during the stance phase (after heel strike) to provide support of the patient, and allows relatively free flexion of the knee joint during the swing phase.

In other embodiments, the knee actuator is an active device that applies a torque to the knee joint to cause a desired flexion of the orthotic frame at the knee joint.

An ankle actuator provides control of dorsal and plantar flexion of the ankle joint, assisting in the correction of problems such as foot slap gait, toe drop, and other problems related to weakness in dorsal or plantar flexors of the foot. As with the knee actuator, both passive and active devices may be employed.

The KAFO is instrumented with a multiple purpose sensor set, which enables measurement of physical variables related to comfort (pressure and strain), kinematics (sagittal plane angles of the knee and ankle joints, rotational velocities of the shank and foot segments, and foot accelerations, for example), and knee joint and actuator status.

Information gathered by the sensor set is used for monitoring purposes and for control of active components of the KAFO. The gathered information may be employed to determine or recognize certain aspects or phases of the gait cycle, and to drive active components of the mechanical orthotic frame to provide assistance at relevant times during the gait cycle. For example, active actuators may help in assisting a patient with muscular weaknesses, such as a patient with weak quadriceps, in regaining functionality.

This intelligent system comprises multiple sensors, such as pressure sensors, strain gauges, angular, sensors, angular velocity sensors, and ground reaction force sensors. Other sensor types may also be included. The information from these sensors is gathered in, and evaluated by, a control unit that in turn controls a set of actuators that activate the KAFO to assist the user. The control function is based on recognizing phases of the gait cycle and responding to strategic needs in the gait cycle to assist the user to maintain "normal" gait cycle.

The sensors and actuators are strategically placed about or near the knee joint, the ankle joint, or at other relevant locations of the mechanical orthotic to provide the relevant information and perform the required assistance during gait.

Also, information gathered is useful during fitting and adjustment of the KAFO. The KAFO allows monitoring of various parameters that provide a basis for tracking activities of the user, which can be helpful in assessment and follow-up of the user.

These and other features, aspects, and advantages of the present invention will become better understood with regard to the following description, appended claims, and accompanying drawings.

BRIEF DESCRIPTION OF THE DRAWINGS

FIG. 6 is a perspective view of the knee actuator of FIG. 4 partially assembled.

FIG. 7 is an exploded perspective view of an ankle actuator according to one embodiment of the present invention.

Similar reference characters denote corresponding features consistently throughout the attached drawings.

DETAILED DESCRIPTION OF VARIOUS EMBODIMENTS

Figures 1, 2:
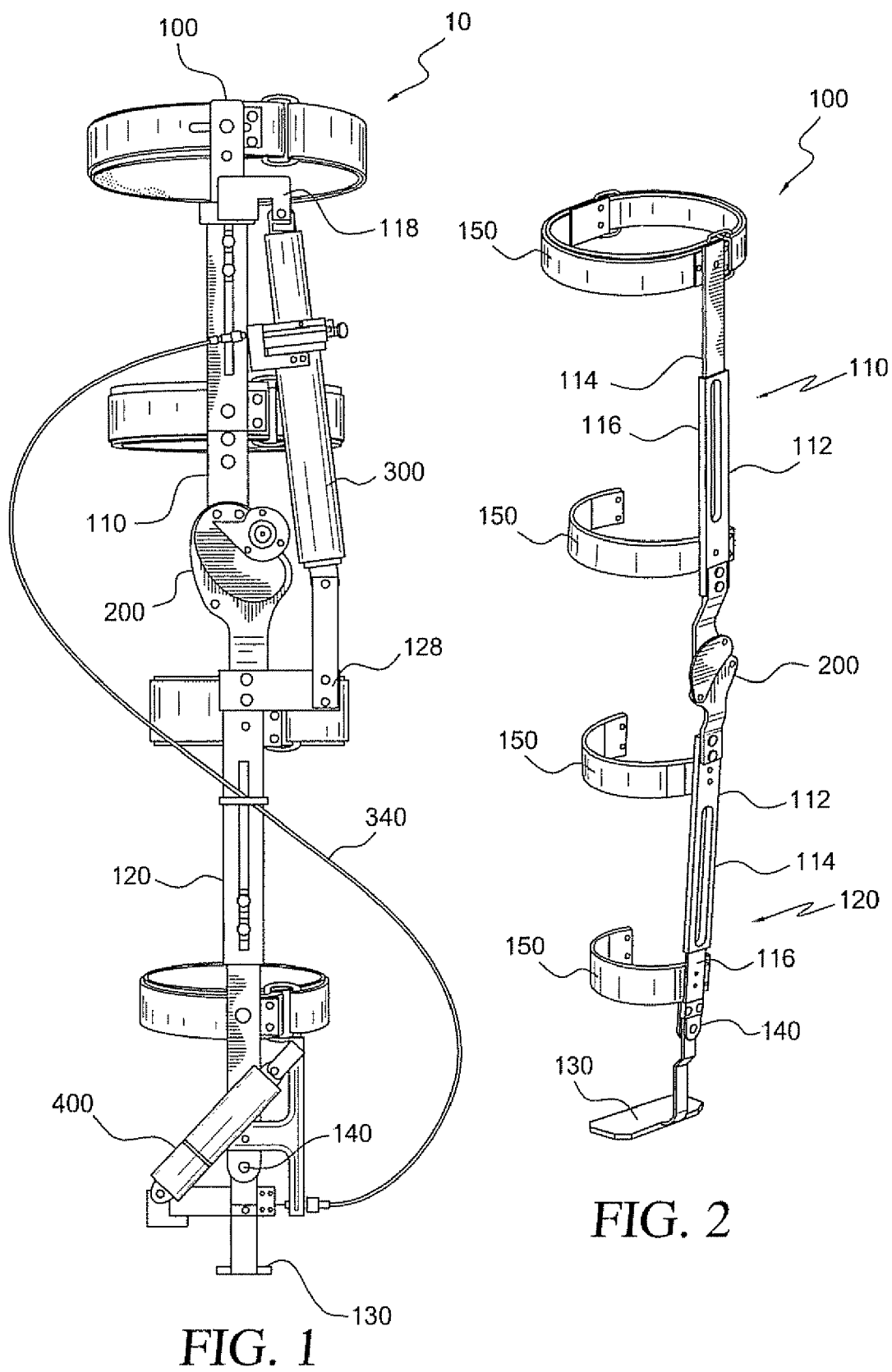
FIG. 1 is a perspective view of an intelligent knee, ankle, and foot orthotic (IKAFO) according to one embodiment of the present invention.
FIG. 2 is a perspective view of an orthotic frame of the IKAFO shown in FIG. 1.

The present invention is an intelligent knee, ankle, and foot orthosis (IKAFO) for biomechanical evaluation and functional compensation of joint disorders. Referring to FIG. 1, an embodiment of an IKAFO is illustrated, designated generally as 10 in the figures. The IKAFO assists a patient suffering from muscular weakness or other problems affecting the patient's gait by providing support and compensation for diminished muscular function or weakness.

The IKAFO 10 shown in FIG. 1 comprises an orthotic frame 100 having an upper or proximal frame 110 and a lower or distal frame 120 joined by a mechanical knee joint 200. A foot support 130 is joined to a distal end of the distal frame 120 by an ankle joint 140.

The orthotic frame 100 is configured to be worn by a user or patient by fitting the upper frame 110 to the upper leg, above the knee, and fitting the lower frame 120 to the lower leg, below the knee, with the knee joint 200 pivotally aligned with the patient's knee. Thus, support is provided to a patient by the orthotic frame 100, while the knee and ankle joints 200, 140 of the orthotic frame 100 allow controlled flexion of the patient's knee and ankle.

Control of the knee and ankle joints 200, 140 by actuators installed on, and working in conjunction with, the orthotic frame 100 allows the orthotic frame 100 to support a patient's weight during certain activities, while also allowing flexion during other activities. Various ambulatory and related activities performed by a person place different requirements on the function of the IKAFO.

For example, while a patient is standing stably, the IKAFO may be required to support the patient's weight, suggesting that the knee joint 200 must be locked or subjected to a high torque so that the orthotic frame 100, and therefore the patient's leg remains extended. Conversely, the knee joint 200 must clearly be allowed to flex freely if the patient desires to sit down comfortably.

Similarly, while a patient is walking, different phases of the walking gait place different requirements on the IKAFO. During a stance phase of the walking gait, for example, the patient's weight is supported by the leg in contact with the ground. As with standing stably, the patient's weight must be supported and a knee joint 200 that is locked or subjected to a high torque contributes to such support. On the other hand, during the swing phase of the gait, it is desirable that the knee joint 200 is allowed to swing freely, or to swing subject to a suitable torque that the knee joint 200 is flexed so that the patient's foot clears the floor. Similar considerations may be recognized with respect to the ankle joint, wherein plantar and dorsal flexion of the may be controlled differently, or subject to different requirements, during different gait phases.

The upper and lower frames 110, 120 of the orthotic frame 100 are fitted to the user's leg with pelotte carriers 150 which are fastened to the user's leg with straps 152 that may be tightened to an appropriate fit.

The upper and lower frames 110, 120 are preferably adjustable in length, to accommodate fitting to patients of different sizes and physical needs. Referring to FIG. 2, the upper and lower frames 110, 120 are each comprised of a side bar or strut 116 that is adjustable in length. Each side bar 112 in the illustrated embodiment comprises an upper and a lower member 114, 116 slidably engaged to one another. Clamping or locking means are provided in the form of a clamp, bolt, or other fastener to lock the upper and lower members 114, 116 together at a desired length.

While the illustrated embodiment employs a single side bar or strut 116 in each of the upper and lower frames 110, 120, alternative embodiments may employ additional side bars or struts, such as a side bar or strut on each side of the patient's leg, a bar or strut located at the front or rear of the leg, or other configurations.

Pelotte carriers 150 are fixed to the upper and lower members 114, 116 respectively, such that the distance between the pelotte carriers 150 is varied according to the length of the side bar 112.

Figure 3:
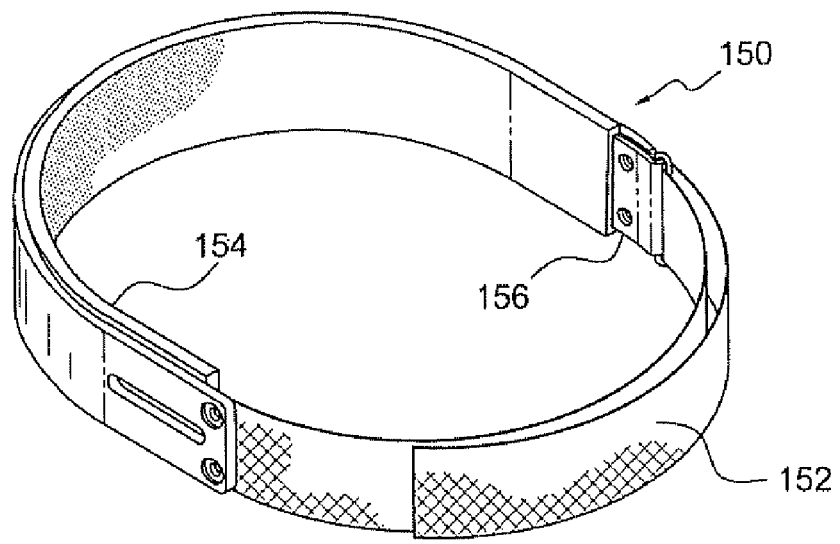
FIG. 3 is a perspective view of a pelotte carrier of the IKAFO shown in FIG. 1.

The illustrated orthotic frame 100 is of a lateral side bar configuration, with the pelotte carriers 150 fastened along the side bars 112. Referring to FIG. 3, the pelotte carriers 150 are in the form of rigid semi-circular or U shaped members configured to be positioned about the front of a patient's leg and secured to the leg by straps 152 extending and secured about the rear of the patient's leg to fasten the orthotic frame 100 in position.

Padding material or cushions 154 are disposed along an inner surface 156 of each of the pelotte carriers 150 to provide for patient comfort as well as fitting. The padding material or cushions 154 may be removable such that proper fitting of the orthotic frame 100 to the patient's leg may be accomplished by fitting a padding material or cushions 154 of an appropriate thickness. Also, the pelotte carriers 150 may be sized for correct patient fit, or bent to accommodate a slightly larger or smaller leg.

The knee joint 200 connects the upper and lower frames 110, 120. Numerous types of orthotic knee joints and hinges are known, including single axis joints, polycentric joints, and others. A single axis joint functions essentially as a simple hinge, allowing for pivoting motion of the upper and lower frames 110, 120 relative to each other about a single, fixed axis of rotation. Polycentric joints incorporate additional rotational axes to allow for a more complex pivoting motion between the upper and lower frames 110, 120. In certain embodiments of a polycentric joint, elements of the joint may be geared or otherwise interconnected so that rotational motion about the various axes is coordinated.

While any type of knee joint or hinge or other rotary element may be used in the IKAFO, it is preferred to employ an orthotic knee joint that accurately models the movement of a human knee about the instant helical axis of the physiological knee.

Figure 4:
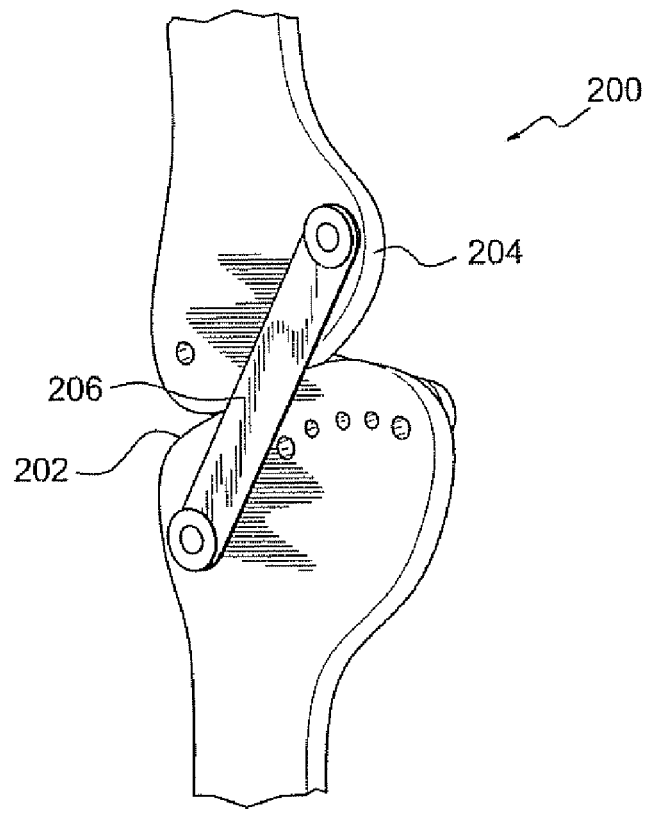
FIG. 4 is a perspective view of a knee joint according to one embodiment of the present invention.

In one preferred embodiment, the knee joint 200 is a four-point knee joint such as one illustrated in FIG. 4 and described in Spanish Patent Application No. 200302322, incorporated herein by reference in its entirely.

The four-point knee joint comprises a fixed lower reference 202 reproducing the physiological curvature of the knee, and an upper follower 204 movably in contact with the lower reference 202. Two levers 206 connect and transmit forces between the lower reference 202 and the upper follower 204. The levers 206 are arranged to guide the movement of the lower reference 202 and the upper follower 204 to reproduce movement according to the physiological curvature of the knee, thereby mimicking flexion of the knee about a variable instantaneous axis of rotation (instantaneous helical axis) of the knee.

The four-point knee joint reduces variations between the movement of the patient's leg and movement of the orthotic frame 100. Accordingly, improvements in patient comfort and gait efficiency are realized.

Patient comfort is improved because reduced variation between the patient and the orthotic frame 100 in movement results in decreased abrasion, or pressure, against the patient by interfaces with the orthotic frame 100, and in a reduction in the necessity for excessively tight attachment of the orthotic frame 100 to the patient.

Gait efficiencies are realized because patient energy expenditures or movements related to compensation for relative movement of the orthotic frame 100 are reduced or eliminated.

Additionally, damage to internal tissues such as ligaments, cartilage, and tendons of the knee joint, is reduced or eliminated because stresses to these tissues caused by the differences in motion of the patients knee joint and the orthotic knee joint are reduced or eliminated.

A knee actuator 300 is disposed on the orthotic frame 100 to control flexion of the knee joint 200, and an ankle actuator 400 is disposed on the orthotic frame 100 to control flexion of the ankle joint 140. The knee actuator controls flexion of the knee joint 200 by providing a variable resistive force against movement of the knee joint 200.

In certain embodiments, the knee actuator 300 is a passive or semi-passive device that provides a fixed, selectable, or variable resistance to the flexion of the knee joint 200. Such a knee actuator 300 may, for example, restrict the flexion of the knee joint 200 during the stance phase (after heel strike) to provide support of the patient, and allow relatively free flexion of the knee joint 200 during the swing phase.

In other embodiments, the knee actuator 300 may be an active device that applies a torque to orthotic frame 100 about the knee joint 200 to cause a desired flexion of the orthotic frame 100 at the knee joint 200.

In the illustrated embodiment, a semi-passive knee joint 300 is employed. The knee joint 300 is referred to as semi-passive since it is not a source of a moving force of the orthotic frame 100 or the knee joint 200, but is adaptable to provide a varied resistance to the movement of the knee joint 200. In other embodiments, an active knee joint may be employed to provide a moving force to the orthotic frame to flex and/or extend the knee joint, compensating further for a patient's muscular weakness, restricted movement, or the like.

The illustrated embodiment employs a single knee actuator 300 provided in the form of a compressible strut extended between the proximal frame 110 and the distal frame 120. The knee actuator 300 is configured to bias the proximal 110 and distal frames 120 of the orthotic frame 100 into an extended or straight legged position. Alternate configurations may be employed for a knee actuator, such as a pair of compressible strut-type actuators disposed on opposite sides of the orthotic frame 100, or alternate types of knee actuator devices incorporated to provide desired torque, bias, or other forces applied to move or influence motion of the orthotic frame 100 components about the knee joint 200.

It is desirable, according to the illustrated embodiment, for the knee actuator 300 to be relatively stiff in compression during the stance phase of the gait cycle, or during certain activities wherein a patient's weight is to be supported by the orthotic frame 100, so that the patient is adequately supported by the orthotic frame 100. On the other hand, it is desirable for the knee actuator 300 to be relatively soft in compression during the swing phase of the gait cycle, or during activities wherein knee flexion is desirable, allowing the patient to bend and extend the knee naturally.

Accordingly, the knee actuator 300 has a selective stiffness or flexion, allowing selection of either of a first compressible stiffness and a second compressible stiffness, so that the knee actuator 300 may provide a relatively rigid compressible stiffness during stance and a relatively flexible compressible stiffness during swing. The knee actuator 300 is provided with a selector 330 that is operable for selecting the relatively rigid or the relatively flexible stiffness.

Figure 5A:
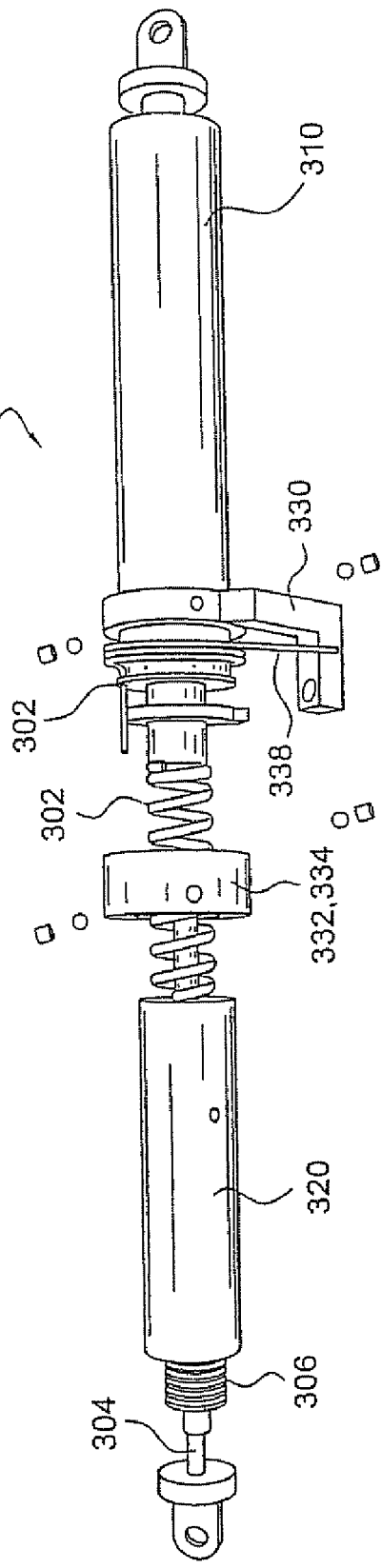
FIG. 5A is an exploded view of a knee actuator according to one embodiment of the present invention.

One example of a knee actuator 300 having a selective compressible stiffness is illustrated in FIGS. 5 and 6. According to the illustrated embodiment, the knee actuator 300 comprises a first cylinder 310, and a second cylinder 320 slidably disposed within a first end 312 of the first cylinder 310. A first spring 302 is disposed within the first cylinder 310 to bias the first cylinder 310 toward an extended position.

A shaft 304 is slidably disposed within the second cylinder 320. A second spring 306 is disposed within the second cylinder 320 to bias the shaft 304 toward an extended position.

It can be recognized that movement of the second cylinder 320 into the first cylinder 310 compresses the first spring 302, while movement of the shaft 304 into second cylinder compresses the second spring 306, thereby providing a first and second compressive stiffness.

While the illustrated knee actuator 300 employs a pair of springs to achieve a selectable compressive stiffness, alternate configurations may be employed such as one or more springs having a variable stiffness, one or more springs supplemented with other means, such as a brake or clutch or other element to selectively lock or damp or otherwise limit the movement of the knee joint 200. Further, spring elements may be replaced with other resilient or compressible members such as hydraulic, pneumatic, or other actuators using a compressible or incompressible fluid, electrical actuators, elements formed from a resilient or compressible material, or the like. The knee actuator may include passive or active components, or a combination thereof.

Additionally, instead of a linear configuration such as the illustrated knee actuator 300, a knee actuator may be configured to employ rotary elements which may be incorporated within a knee joint or elsewhere on the orthotic frame 100.

The knee actuator 300 may be further altered to provide additional selectable compressive stiffness settings, or may be configured such that a continuously variable compressive stiffness is provided. Such additional selectable compressive stiffness settings may be achieved by providing additional cylinder and spring combinations in the manner illustrated, or otherwise according to the above discussed alternatives.

Figure 5B:
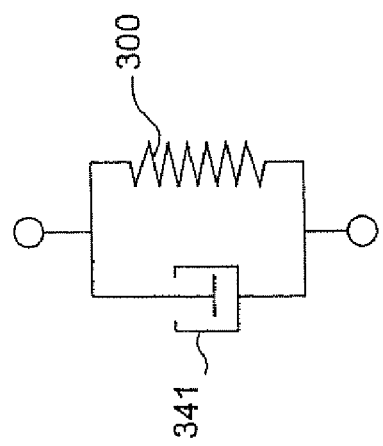
FIG. 5B is a schematic representation of a damped knee actuator.

The knee actuator 300 may also be provided with one or more damping element, such as a damper 341 as shown in FIG. 5B.

As configured in FIG. 1, a connecting member 305 of the shaft 304 is attached to a mounting support 118 on the upper frame 110, and a connecting member 314 of the first cylinder 310 is attached to a mounting support 128 on the lower frame 120.

The first spring 302 is a relatively soft spring, while the second spring 306 is relatively stiff. Thus, by selectively enabling the first 302 or the second 306 spring, the knee actuator 300 provides a relatively soft or a relatively stiff compression, respectively.

The selector 330 is in the form of a locking mechanism provided to selectively activate or enable the first spring 302. The locking mechanism comprises a locking collar 334 located, in one embodiment, at the first end 312 of the first cylinder, and disposed about the second cylinder 320.

One or more longitudinal tracks 322 are formed on the surface of the second cylinder 320. The tracks 322 each accommodate a ball 336 which can move freely along the track 322. A locking detent 324 is provided alongside each track 322, and the locking detents 324 are each located at a same distance from the end of the second cylinder 320.

The balls 336 are retained within the tracks 322 by the locking collar 334, and the balls are movable by the locking collar 334 into the locking detents 324 when the second cylinder 320 is positioned such that the balls 336 within the locking collar 334 are aligned with the locking detents 324.

When the balls 336 are moved into the locking detents 324 by the locking collar 334, the second cylinder 320 is prevented from movement relative to the first cylinder 310. Accordingly, when the second cylinder 320 is locked in place by the locking mechanism, the knee actuator 300 is compressible according to the relatively stiff second spring 306. Conversely, when the second cylinder 320 is unlocked, the knee actuator 300 is compressible according to the relatively soft first spring 302.

Thus, moving the locking collar 334 allows selection of either of a relatively flexible mode (according to the first spring 302) and a relatively stiff mode (according to the second spring 306).

The locking collar 334 may be provided with a torsion spring 338 to bias the locking collar 334 toward its locking position, such that the second cylinder 320 will become automatically locked in position when the locking detents 324 become aligned with the balls 336 of the locking collar 334.

According to one configuration, the locking detents 324 are positioned such that the locking position of the second cylinder 320 is at or near the maximum extension of the second cylinder 320 from the first cylinder 310.

When the knee actuator 300 of this configuration is disposed between the lower 120 and upper 110 frames of the orthotic frame 100, the locking position of the knee actuator 300 corresponds to the maximum extension, or straight legged position, of the orthotic frame 100.

Accordingly, locking the knee actuator 300 when the orthotic frame 100 is in the straight legged position causes flexion of the knee joint 200 to be subject to the relatively stiff second spring 306, limiting flexion of the knee joint 200 and providing support for the patient.

While the knee actuator 300 is locked, the knee joint 200 itself is not locked, but is instead movable subject to the relatively stiff second spring 306 of the knee actuator 300. Therefore, shock absorption is provided during the stance phase of the gait by flexion that is permitted by the second spring 306.

It is desirable for the knee actuator 300 to be locked, or in a stance state, to provide the limited flexion of the relatively stiff second spring 306 during the stance phase of the gait cycle so that the patient is adequately supported in stance by the orthotic frame 100. Similarly, it is desirable for the knee actuator 300 to be unlocked, or in a swing state, during the swing phase of the gait cycle, so that the knee joint 200 of the orthotic frame 100 may be flexed subject to the relatively soft first spring 302, allowing knee bend and extension of a natural gait during the swing phase.

It is desirable for the selector 330 to produce an audible sound, such as a clicking sound, when the selector 330 is moved into at least one of the locked and unlocked positions, to provide an audible feedback to the user. For example, if the selector 330 is configured to produce a click when the knee actuator 300 is locked, the user may rely on the click as a signal that the knee actuator 300 is locked and the IKAFO 10 will support the user. Conversely, if no sound is heard, the user recognizes an "unsafe" condition and may take a remedial action such as relying on crutches, a cane, or the like for support.

A control element is connected to the selector of the knee actuator 300, and is configured to move the selector 330 between the first and second position according to at least one aspect of a walking gait cycle, or one aspect of an ambulatory or related activity. For example, it is desirable for the relatively stiff second spring 306 of the knee actuator 300 to be selected during the stance phase of the patient's walking gait, so that the patient is supported by the orthotic frame. Similarly, it is desirable for the relatively flexible first spring 302 of the knee actuator to be selected during the swing phase of the patient's gait so that the leg may swing forward with the knee bent in the manner of a normal, natural gait.

In one embodiment, the control element allows selection of the stiffness of the knee actuator 300 according to the angle of flexion of the ankle. Because the angle of flexion of the ankle (and thus of the ankle joint 140) varies generally predictably during the course of a normal walking gait, the angle of flexion of the ankle may be used to determine, at least roughly, certain phases or points during the gait.

In a simplified approach, when the ankle reaches a predetermined position of dorsal flexion, the selector 330 of the knee actuator 300 is activated to select the relatively flexible first spring 302, making it possible for the patient to bend the knee. Subsequently, when the knee is extended later in the gait cycle (and the knee actuator 300 reaches its extended position), and when the ankle has returned to a less dorsally flexed position, the knee actuator 300 is locked leaving the relatively stiff second spring 306 active.

For example, it can be recognized that the ankle typically reaches a maximum degree of dorsiflexion just prior to toe-off, indicating the end of the stance phase. Accordingly, this may provide a cue to release the knee joint 200 by selecting the relatively flexible compressible stiffness of the knee actuator 300. Moving the selector 330 according to the ankle dorsiflexion allows setting the knee actuator 300 accordingly so that the knee joint 200 is free to flex during the swing phase.

Conversely, as the ankle plantarflexes somewhat during the swing phase, the selector 330 may be moved accordingly such that when the leg reaches full extension at the end of the swing phase, the knee actuator 300 will be locked, providing the support of the relatively stiff compressible stiffness of the knee actuator 300 during the subsequent stance phase.

This simplified approach to selecting the stiffness of the knee actuator 300 may be accomplished by an entirely mechanical arrangement, wherein the control element comprises a cable 340 or cable pushrod or the like connected between the ankle or the foot plate and the selector 330 of the knee actuator 300. The cable 340 is movable according to the angle of the ankle, so that when the ankle or foot plate reaches a certain degree of dorsal flexion, the cable 340 operates the selector 330 to unlock the knee actuator 300 and activate the flexible setting of the knee actuator 300.

Since the ankle is biased toward a neutral position (in neither dorsal nor plantar flexion), it follows that the dorsal flexion of the ankle decreases after toe-off and during the swing phase. Thus, the selector 330 is returned into the position for activating the stiff setting of the knee actuator so that when the leg is straightened at the end of the swing phase the stiff setting of the knee actuator is activated.

Typically, the cable will be adjusted to activate the flexible setting of the knee actuator 300 when the dorsal flexion of the ankle is at, or approaching, a maximum toward the end of the stance phase of the gait cycle (just before toe-off). With the flexible setting of the knee actuator 300 activated, the patient's knee is allowed to flex under the patient's weight at the end of the stance phase, as the patient's other leg approaches heal strike and the beginning of the stance phase to support the patient.

The cable may be adjusted differently to suit different patient needs, or different gait issues.

In an electro-mechanical approach to changing the biasing force of the knee actuator 300, a control element comprises a solenoid 342 to operate the selector 330 according to an electronic control signal. The solenoid 342 is driven by an electronic control signal which may be generated from an electronic measurement of the flexion of the ankle or from other information.

The control signal may be derived simply from measurement of the dorsal flexion of the ankle, functioning similarly to the mechanical approach except replacing the function of cable 340 the solenoid 342, a sensor for measuring the ankle flexion, and an electronic circuit to interpret the sensor and generate the control signal.

Alternatively, the control signal may be derived from information derived from additional sensors disposed on the orthotic frame 100, as well as tuning factors provided during a fitting or adjustment process to more precisely identify a correct position during the gait cycle to reduce the knee stiffness. The control signal may also be derived from a user switch or control 880 that allows the user to override automated generation of the signal, for example to continuously lock the knee actuator 300 during a stair climbing or descending activity.

An ankle actuator 400 is disposed on the orthotic frame 100 to control flexion of the ankle joint 140, and to provide assistance or compensation for muscular function related to dorsal and plantar flexion of the foot. The ankle actuator 400 allows partial storage of elastic energy during dorsal flexion of the foot and recovery of the stored energy during plantar flexion of the foot to avoid drop foot.

In an embodiment of FIG. 7, an ankle actuator 400 comprises a single shaft 410. A stopping member 416 is disposed on the shaft 410 proximate to a coupling fitting 414 at a first end 412 of the shaft 410 and a sliding member 402 is slidably disposed on the shaft 410.

A first spring 404 is disposed on the shaft 410 between the stopping member 416 and the sliding member 402, and a second spring 406 is disposed on the shaft 410 on the side of the stopping member 416 of a second end 418 of the shaft 410.

The shaft 410 is movably contained in a cylindrical housing 420 with the first end 412 of the shaft 410 extending from a first end 422 of the housing, and the stopping member 416 is fixed to the housing 420. In the illustrated embodiment, the cylindrical housing 420 comprises a first housing half 424 and a second housing half 426 which are coupled to opposite sides of the sliding member 402 of the shaft 410.

Referring to FIG. 1, the ankle actuator 400 is shown coupled between the lower frame 120 and the foot support 130, with the coupling fitting 414 attached to a mounting support 129 on the lower frame 120 and a coupling fitting 419 of the cylindrical housing 420 attached to a mounting support 132 on the foot support 130 or a lower member of the ankle joint 140.

It can be seen that the ankle actuator 400 provides different torques to the ankle joint 140 according to the selection of the first 404 and second 406 springs, so that the ankle actuator 400 may be configured for assistance or compensation in either, or both, of dorsal and plantar flexion of the foot.

As discussed above with respect to the knee actuator 300, the ankle actuator 400 may be alternatively embodied. Various passive or active configurations may employ rotary or linear elements, including hydraulic, pneumatic, or other actuators using a compressible or incompressible fluid, electrical actuators, and elements formed from a resilient or compressible material, or the like. The ankle actuator may include passive or active components, or a combination thereof.

Figure 8:
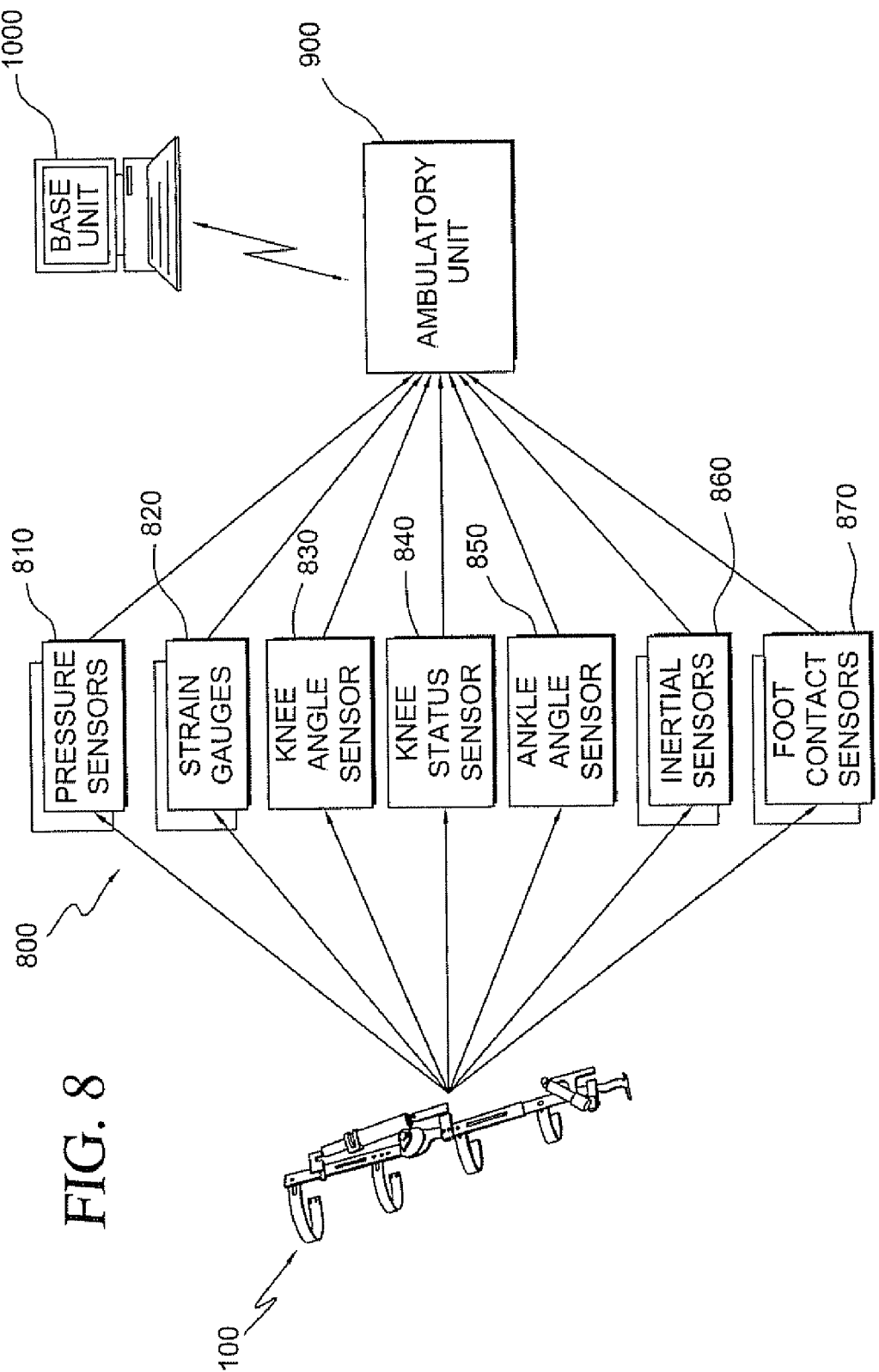
FIG. 8 is a block diagram identifying instrumentation applied to the orthotic frame in one embodiment of the present invention.

Referring to FIG. 8, the IKAFO is instrumented with a multiple purpose sensor set 800, which enables measurement of physical variables related to comfort (pressure and strain), kinematics (sagittal plane angles of the knee and ankle joints, rotational velocities of the shank and foot segments, and foot accelerations, for example), knee joint and actuator status, and other events related to ambulatory and related activities, including aspects of the gait cycle such as initial foot contact, foot flat, heel off, and toe off.

Data gathered from the sensor set 800 may be analyzed for biomechanical evaluation of the patient's use of the IKAFO, which may be useful for fitting of the IKAFO as well as monitoring the patient's progress and diagnosing problems with the patient relating to the IKAFO.

Further, real-time analysis of the data from the sensor set 800 allows identification of ambulatory and related activities that are performed by the patient, and can contribute to functional compensation provided by the IKAFO. For example, while control of the knee actuator 300 was described above with respect to ankle flexion, it can be recognized that a broader range of compensation strategies may be employed based on recognition of different activities such as sitting down, standing up, walking up or down stairs or a slope, or other activities that may place different requirements on the functionality of the IKAFO.

The sensor set may include pressure sensors 810, strain gauges 820, a knee angle sensor 830, a knee status sensor 840, an ankle angle sensor 850, inertial measurement units (IMUs) 860, and foot contact sensors 870. An ambulatory data processing unit (ambulatory unit) 900 is co-located with the IKAFO (mounted to the orthotic frame 100 or carried by the patient, for example), to monitor the sensors and to process sensor data to control actuators of the IKAFO. The ambulatory unit 900 also provides data communication to a base unit 1000 where further analysis of the sensor data may be performed.

Pressure sensors 810 are disposed on portions of the orthotic frame 100 that interface directly with a patient. Pressure sensors 810 may be located on the pelotte carriers 150, such as between the pelotte carrier 150 and a padding material or cushion 154. In one embodiment, the pressure sensors 810 are strain gages, located on the lateral aspect of each pelotte carrier 150 and protected against mechanical interactions and environmental factors.

Additionally, strain gauges 820 may be disposed on the orthotic frame 100 to measure stresses on the components of the orthotic frame 100 that are related to various ambulatory activities. Strain gauges are applied to the side bars 112 of the upper and lower frames 110, 120 to measure deformation of the side bars 112 that are related to loading of the side bars 112 during various ambulatory activities, to provide a measurement of the loading.

A knee joint angle sensor 830 is disposed on or proximate to the knee joint 200, and is configured to measure the knee angle (an angle between the proximate and distal frame portions). In one embodiment, the knee joint angle sensor 830 is a precision potentiometer mounted on attaching members of the knee joint 200 to measure the angle in one axis of the knee hinge.

An actuator lock mechanism sensor 840 is a sensor disposed on or proximate to the knee actuator 300 to sense the lock/unlock status of the actuator lock mechanism. In one embodiment, the actuator lock mechanism sensor 840 is a contact switch disposed to determine the lock/unlock status of the actuator lock mechanism based on the position of the actuator lock mechanism.

The actuator lock mechanism sensor 840 is useful, in addition to simply gathering information for biomechanical evaluation of the IKAFO or the patient, to provide an audible or other signal or warning relating to the lock status of the knee actuator 300. For example, a signal may be generated to indicate to the patient that the knee actuator 300 has been locked, so that the patient can confidently rely on the IKAFO to support her weight. Similarly, an alarm may be generated if a control signal has been sent to lock the knee actuator 300, but the locking mechanism is not properly activated.

Inertial measurement units (IMUs) are provided on the shank (lower frame 120) and foot parts of the orthotic frame 100. A foot IMU 860 is positioned below the ankle joint and a shank IMU 860 is located along the lower (or shank) frame portion 120. The foot IMU 860 may be contained within a housing or small box disposed below the ankle joint, and the shank IMU 860 may be collocated with other electronics or interconnections in a junction or interconnection box located along the shank (distal) frame portion. Each of the IMUs 860 comprises a rate gyroscope and a biaxial accelerometer.

In addition, or alternatively to the IMUs (and other sensors), one or more linear accelerometers may be employed to sense movement or kinematic information of any of the moving parts of the orthotic frame 100. It can be recognized that such linear accelerometers may be employed to provide movement or kinematic information that is unavailable from, or that is redundant to, other sensors.

Foot contact sensors 870 are provided on the foot plate 130 in the form of pressure sensors or contact switches to detect foot contact with the ground. Foot contact sensors 870 are located at both front and rear parts of the foot plate 130, to detect both toe (or fore foot) and heel (or rear foot) contact events. The foot contact sensors 870 may be disposed between the foot plate 130 and a soft insole.

Alternative to foot contact sensors 870 provided on the foot plate 130, pressure or contact or other types of sensors may be deployed elsewhere on the orthotic frame 100 to sense foot contact status such as foot strike or lift or related events. For example, accelerometers may detect motion or impact associated with foot strike or lift events, and strain gauges positioned variously about the orthotic frame may provide information relating to the loading of the orthotic frame that may be associated with foot strike and lift events.

Other types of sensors may be used in addition to, or in place of, those described. For example, Global Positioning System (GPS), magnetic flux, or other types of sensors may be employed to provide movement or kinematic information that is unavailable from, or that is redundant to, other sensors.

The ambulatory unit 900 gathers kinematic information from the various sensors disposed on the orthotic frame 100. The kinematic information may be processed locally by the ambulatory unit 900, and may be used to control actuators (such as the knee actuator 300) of the IKAFO in response to events or conditions that are detected or recognized by the ambulatory unit 900 based on analysis of the kinematic data. The ambulatory unit 900 also provides an interface for forwarding gathered data to the base unit 1000 for further processing and analysis.

Figure 9:
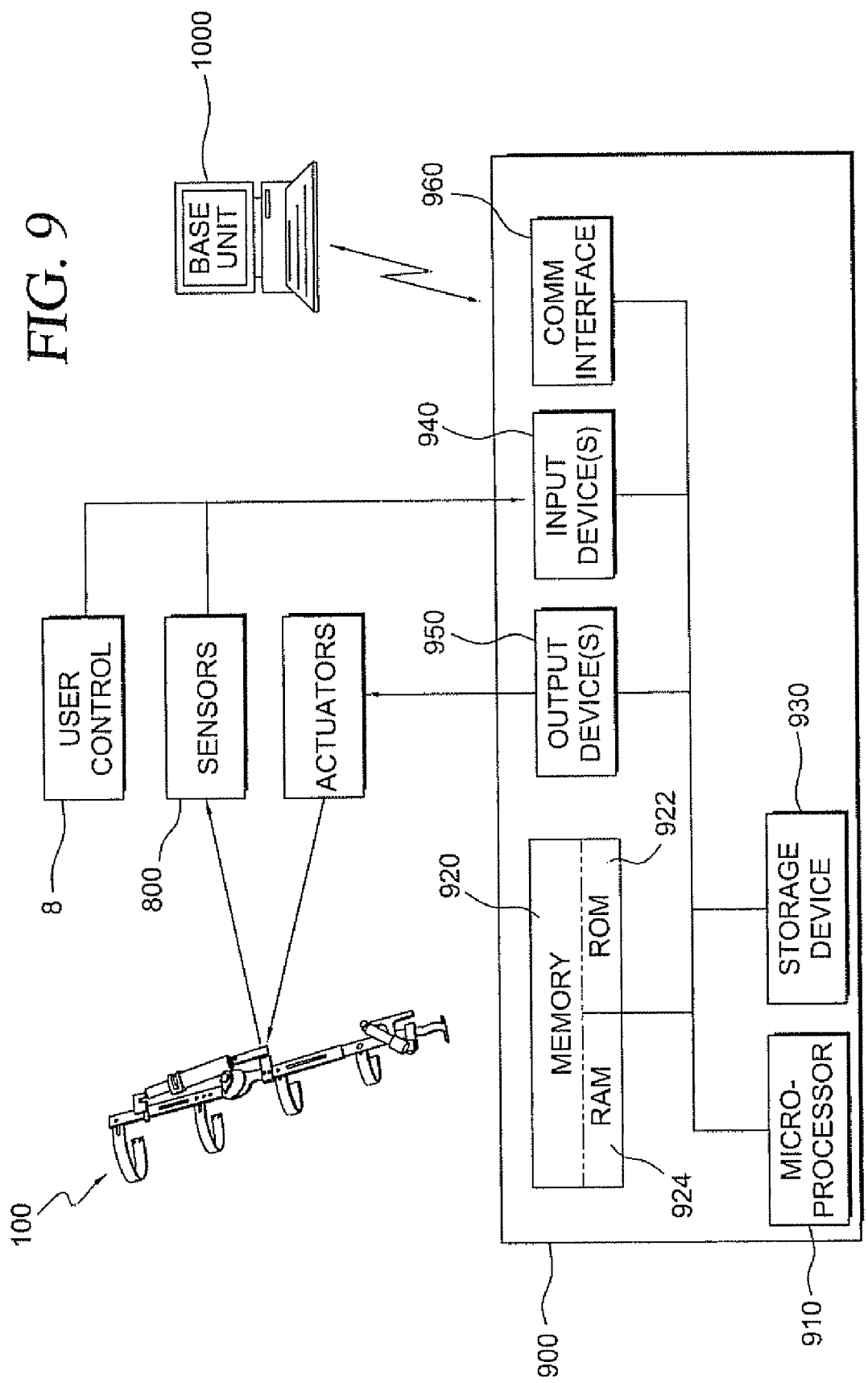
FIG. 9 is a block diagram of an ambulatory control unit for a KAFO according to an embodiment of the present invention.

Referring to FIG. 9, the ambulatory unit 900 comprises generally conventional control hardware architecture. Such a control hardware architecture typically comprises a microprocessor 910 connected by a bus 990 to an area of main memory 920, comprising both read only memory (ROM) 922, and random access memory (RAM) 924.

The microprocessor 910 may be in communication, via bus 990, with a storage device 930 such as a disk storage device or a removable media memory device such as a removable memory card or the like. Input/output devices 940, 950 are included to provide an interface to the sensors and actuators of the IKAFO 10.

A communication interface 960 is provided for communication between the ambulatory unit 900 and the base unit 1000. The communication interface 960 may be a wireless interface, employing an RF, infra-red (IR), or other wireless communication medium. Alternatively, the communication interface 960 may be wired, using a cable in connection with the base unit 1000.

A control program may be stored in the ROM 922, or loaded into memory 920 from storage device 930, for execution by the microprocessor. The control program functions to read sensor data from the sensor inputs, and to evaluate the sensor data for control of actuators of the orthotic frame 100. The control program also may store the sensor data in the storage device 930 for later recall and transmission to the base unit 1000, or transmit the sensor data to the base unit 1000 in real time.

The control program thus reads sensor data for both real-time control of the IKAFO 10 and for later analysis in the base unit 1000. Sensor data sampling rates for real-time functions are typically higher than sampling rates for later analysis. For example, a sampling rate of 100 Hz may be employed for real-time control functions, while a sampling rate of 30 Hz may be employed for data that is merely to be stored for later analysis at the base unit. For data storage, it can be recognized that data rate and the capacity of the storage device 930 influence the amount of information that may be recorded for later analysis.

In the electro-mechanical approach to changing the biasing force of the knee actuator 300, a control program executed by the ambulatory unit 900 determines when to signal the knee selector 330 to select the rigid setting or the flexible setting. While a simple control program may be employed to mimic the mechanical activation of the knee actuator 300, by simply measuring the angle of flexion of the ankle and unlocking the knee actuator 300 at a predetermined angle, a more advanced control program is a rule-based detection algorithm for the cycle-to-cycle selection of the knee actuator 300 setting based on a more comprehensive sampling of kinematic data of the orthotic frame 100.

Input signals form the sensors are periodically sampled as inputs to the control program. The control program may consider the knee angle, the ankle angle, the angular velocity of the shank (lower frame 120), the current status of the knee actuator 300 (locked or unlocked), as well as other information.

Figure 10:
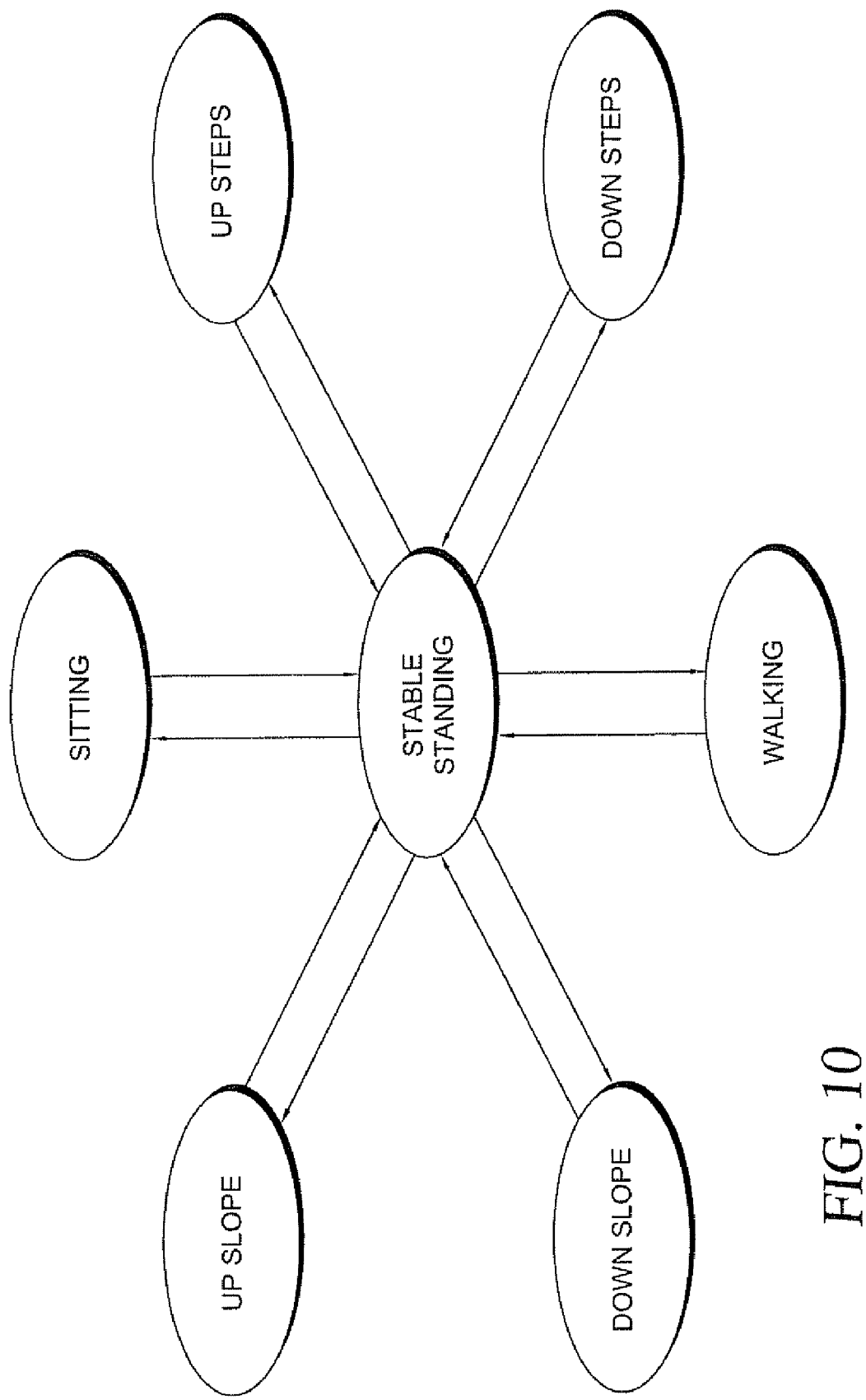
FIG. 10 is a state transition diagram depicting transitions between activity states.

Data collected from the sensors may be interpreted to identify transitions between various, discrete, ambulatory activities or states. Referring to FIG. 10, such transitions include transition from standing stable to walking, and from walking to standing stable. Other transitions include sitting to standing stable and standing stable to sitting, and commencing or ending walking uphill, downhill, up steps, or down steps. Additionally, the sensor data may be interpreted to detect gait events such as initial contact of the foot (heel strike), full foot contact (mid-stance), lifting of the heel, and toe-off.

Figure 11A:
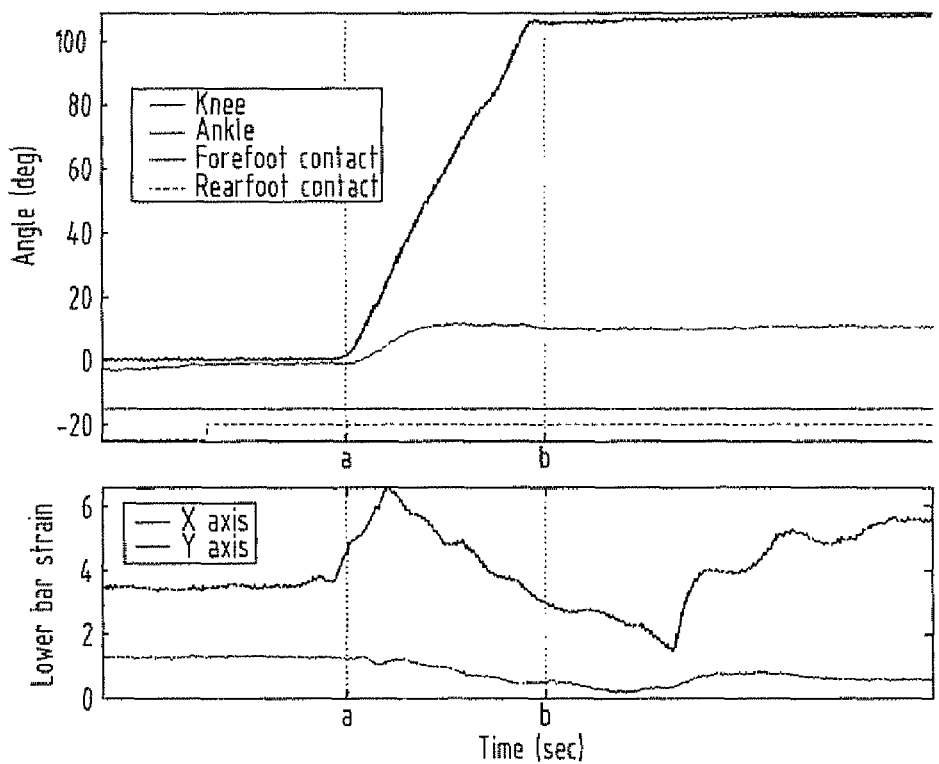
FIG. 11A is a graph depicting measured sensor data during an activity of sitting down from a standing position.
Figure 11B:
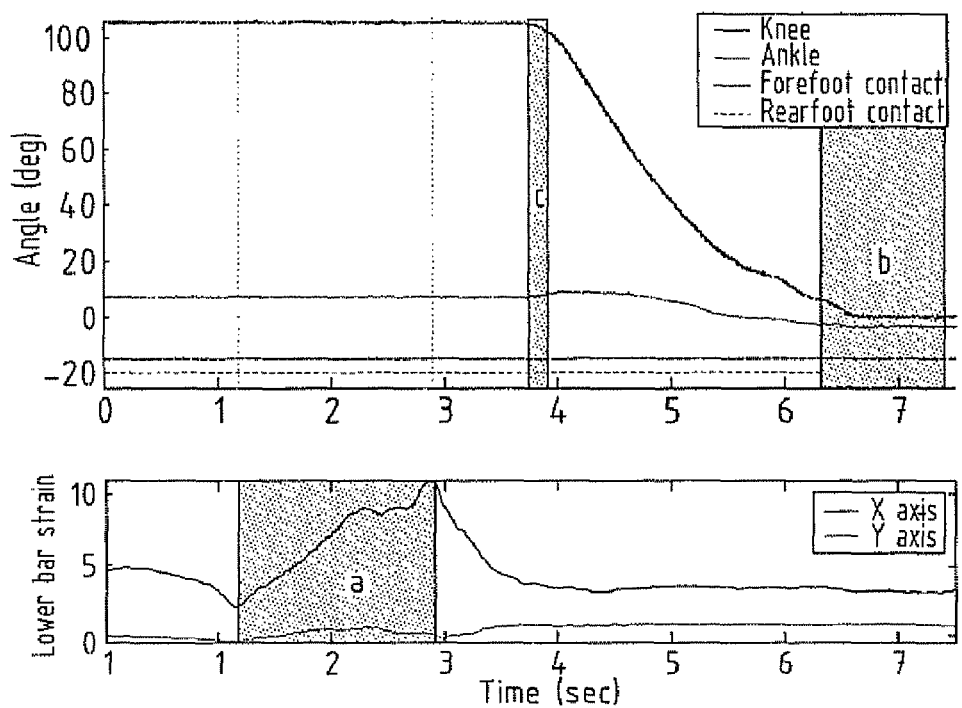
FIG. 11B is a graph depicting measured sensor, data during an activity of standing up from a seated position.

Data collected during trials of sitting down and standing up activities are shown in FIGS. 11A and 11B. Each figure shows measured data from a single transition (between standing to sitting, and vice versa). Knee joint angle data gives a direct indication of these transitions. Additionally, foot contacts and structural deformation of the side bar give information that may be used for prediction of the subject's intention to start the transition. For example, information about loads generated through the frame by muscle activity before motion is achieved may be predictive of a subject's intention to stand or to sit.

It can be seen with reference to FIG. 11A that, while sitting down from an upright (stable standing) position, certain features can be identified by observational analysis: 1) torque at the lower bar X-axis increases (positive torsion moment) when knee flexion starts, and the knee joint velocity increase significantly as is apparent from the slope of the knee angle curve; 2) knee joint velocity stabilizes approximately at 100° of flexion, and X axis torque approximately reaches a neutral value; 3) the thigh segment (upper frame 110) begins to accelerate significantly (counter clock-wise), and changes its vertical orientation with respect to ground; and 4) foot contact sensors indicate contact and then non contact since the subject is trained to sit using his/her non-orthotic leg.

Similarly, as the subject begins to stand up (referring to FIG. 11B), recognizable features include: 1) a significant increase in X-axis deformation (torsion moment), at the lower bar of the orthosis, followed by a decrease, appears when the subject initiates the transition and before other motion information indicates this (so that, as with the standing to sitting transition described above, loading information gives advanced information about the subject's intent); 2) the knee begins to extend from a flexion of around 100°; 3) the knee ends at full extension, coincident with ankle flexion a neutral position, when the subject is standing stable; 4) the thigh segment (upper frame 110) begins to accelerate significantly (clock-wise) and changes its horizontal orientation with respect to the ground; and 5) given that the correct starting position supposes that ankle is in dorsiflexion, while putting weight on the rear part of the foot contact sensors at the heel would be pressed.

Accordingly, it can be recognized that processing and analysis of the sensor data can result in accurate recognition of activities performed by a patient wearing the IKAFO 10, based on rules derived from the measured and expected sensor data during transition from one activity (or state) to another.

In addition to the activities of sitting down and standing up, other activities of interest include initiating and stopping walking, and transitions to and from walking upslope and downslope, and transitions to and from walking up and down steps.

Figure 12A:
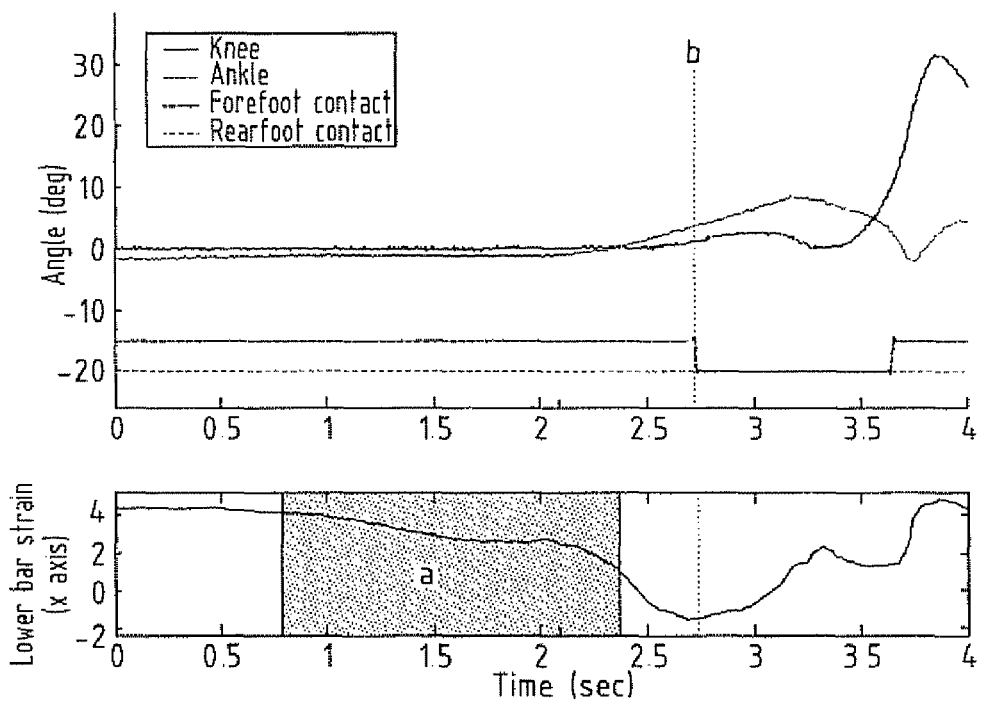
FIG. 12A is a graph depicting measured sensor data during an activity of beginning to walk (transitioning from standing stable to walking).
Figure 12B:
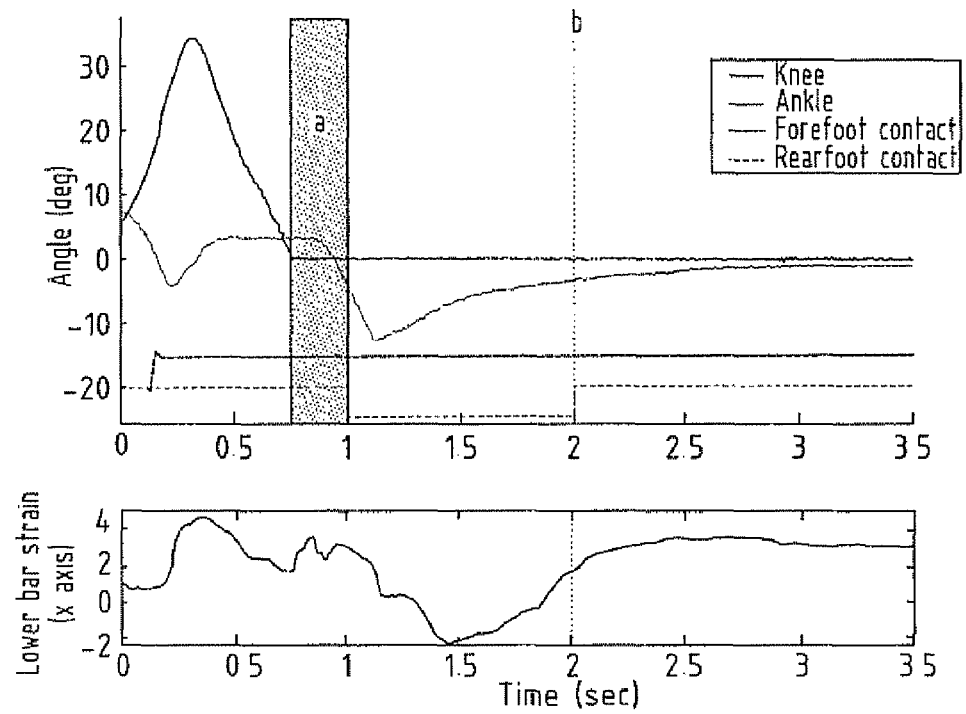
FIG. 12B is a graph depicting measured sensor data during an activity of stopping walking (transitioning from walking to standing stable).

Data collected during trials of start walking and stop walking activities are shown in FIGS. 12A and 12B. In starting walking (gait initiation) from stable standing (referring to FIG. 12A), a negative strain related to torsion moment at the lower frame 120, is measured before joints motion begins, and can give "predictive" information of subject's intention to initiate gait. Heel off occurs at the start of gait initiation, and is indicated by foot contact sensors 870 indicating no contact by the rear of the foot, and contact by the front of the foot. Ankle dorsiflexion begins at heel-off.

The foot begins to accelerate faster than other segments. Knee flexion starts after ankle dorsiflexion.

As the heel rises, the foot segment tilts with respect to ground. The shank and thigh (lower and upper frames 110, 120) both tilt significantly indicating the beginning of the transition.

In stopping walking (transitioning from walking to stable standing) (referring to FIG. 12B), the knee angle stabilizes at full extension while decelerating. The ankle joint reaches a neutral position from a dorsiflexion trajectory.

The knee is held at full extension during a short transient, while the ankle is still in plantar flexion. A delayed heel strike event is detected in comparison with a continued gait pattern. Torsion moment trends to stabilize to a static situation.

Figure 13A:
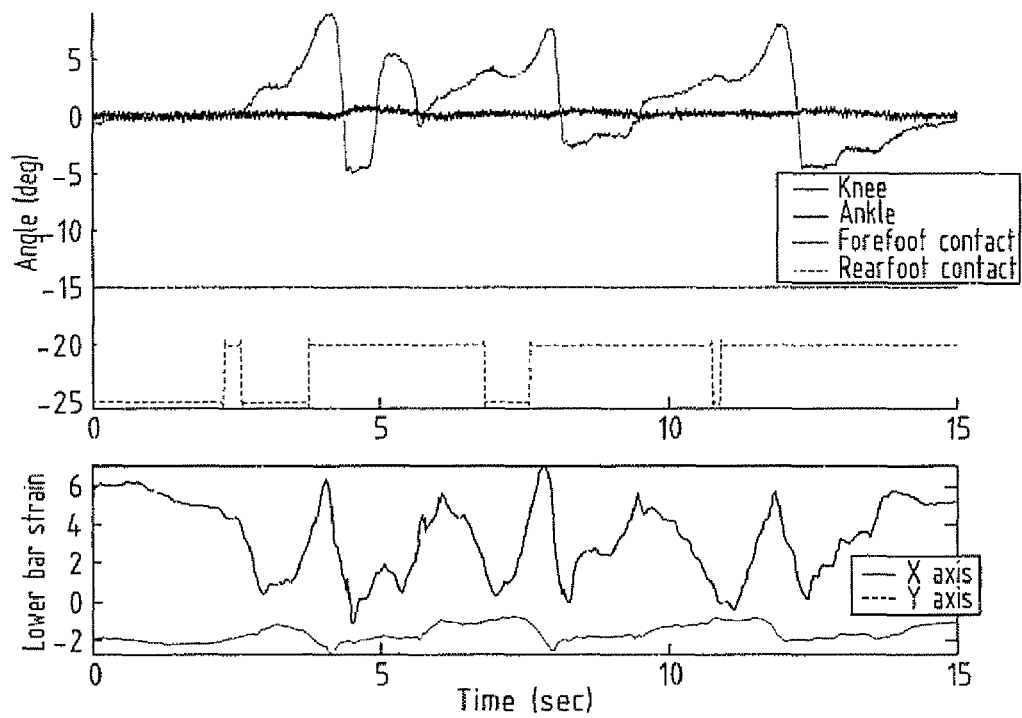
FIG. 13A is a graph depicting measured sensor data during a walking up stairs activity.
Figure 13B:
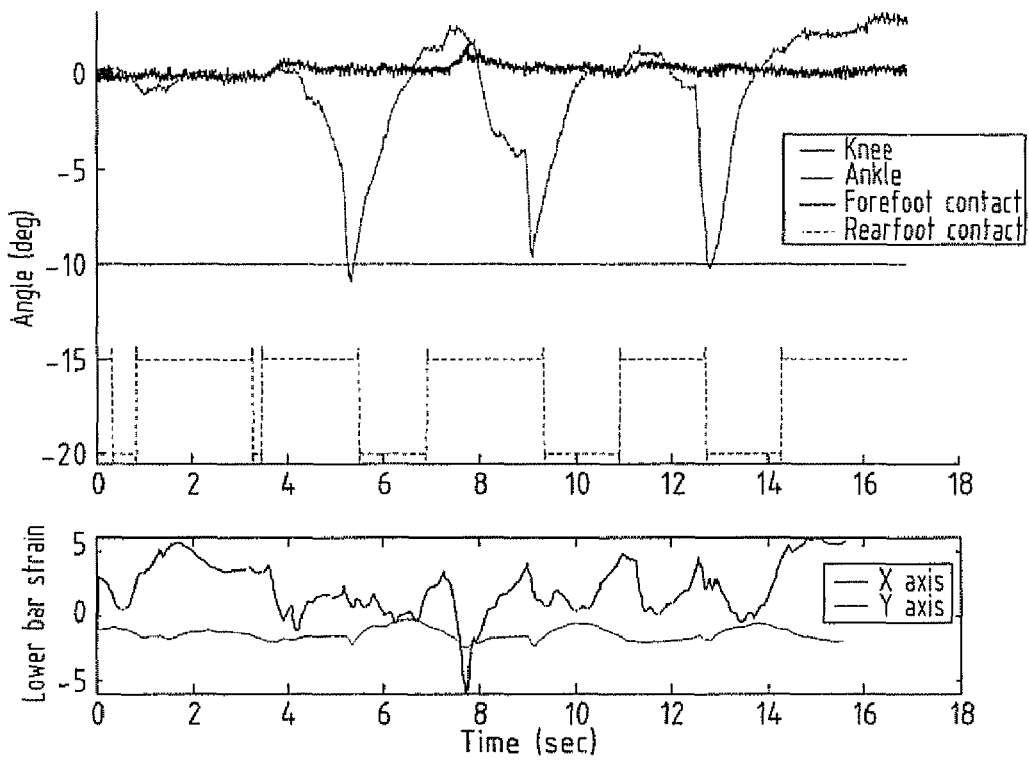
FIG. 13B is a graph depicting measured sensor data during a walking down stairs activity.

Data collected during trials of going up and down stairs are shown are shown in FIGS. 13A and 13B, respectively. Signals from sensors were measured during negotiating three stair steps up and down. The knee joint was locked during these activities.

While negotiating stairs, ankle joint angle and strains recorded at the x-axis of the side bar 112 of the lower frame 120 give the most valuable information among the data shown in the figures. While knee joint is locked during these activities, tilt information of the upper and lower frames 110, 120 is not primal, but foot segment tilt as related with ankle joint relative angle and velocity provides information about the progression of this activities. Foot contact sensor activation is quite variable and dependant on the way the subject deals with each tread, so this information is considered as supporting but not essential for this detection.

Figure 14A:
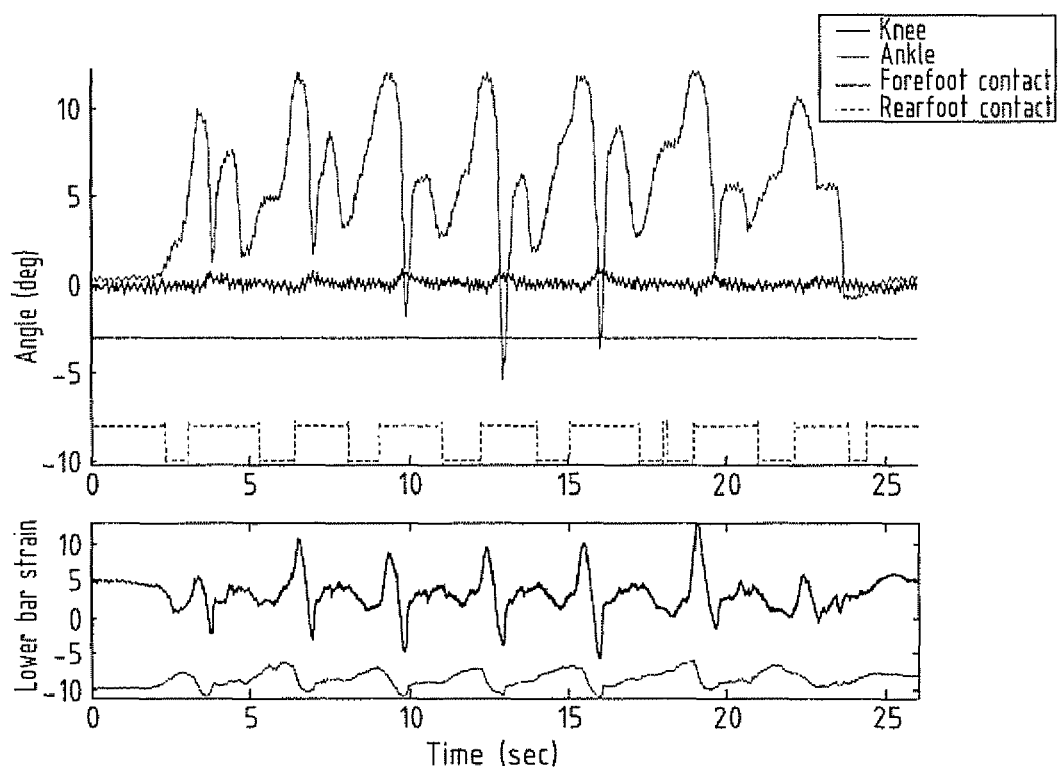
FIG. 14A is a graph depicting measured sensor data during an upslope walking activity.
Figure 14B:
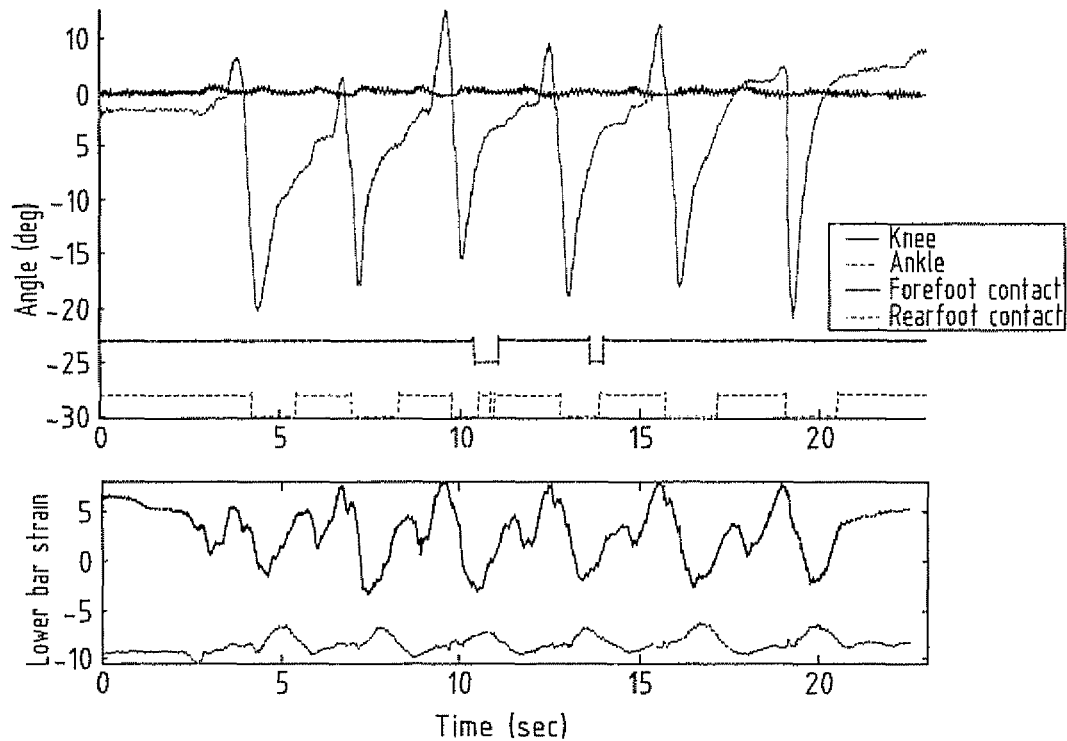
FIG. 14B is a graph depicting measured sensor data during a down slope walking activity.

Data collected during trials of walking up and down a slope are shown are shown in FIGS. 14A and 14B, respectively.

Ankle joint angle data discriminates clearly between both transitions (level to up slope and level to down slope). Also, deformation along the perpendicular axis of the side bar 112 of the lower frame 120 features high peaks distinguishable from those present during level walking. Correlation of the side bar deformation and the ankle angle provides a lot of knowledge about the upslope and downslope activities. Foot contact sensor information is not reliable during up and down slope walking due to drastic changes in the way the subject applies foot load over the sloped surface.

The activities and transitions are generally considered to each begin and end in the stable standing state. Accordingly, it is desirable for the stable standing state to be well defined by the available signals. The static, stable standing state may be features such static conditions (no angular velocities or accelerations of the upper and lower frames 110, 120 and ankle and knee joints 140, 200). The knee is generally fully extended, and the ankle joint at a neutral position (within a +/−5° range). The upper and lower frames 110, 120 are in a vertical position, and the foot support is in a horizontal position. The heel and toe both contact the ground, and mean pressure at fore and rear foot zones trends to stabilize.

Figure 15A:
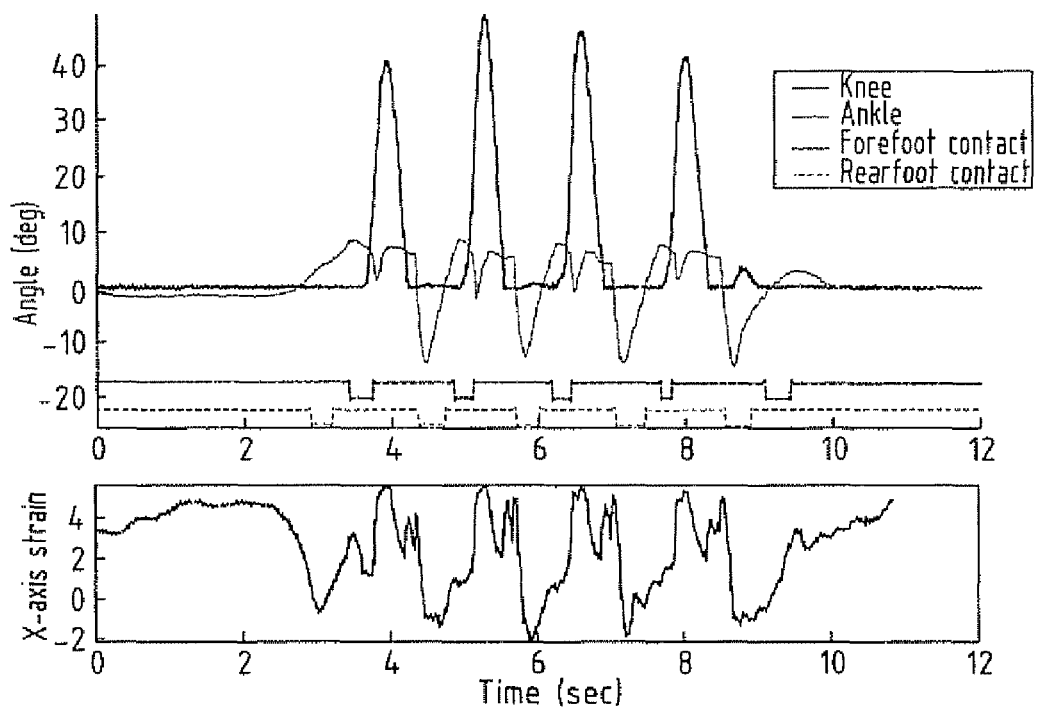
FIG. 15A is a graph depicting measured sensor data during a walking activity, showing data for four walking gait cycles according to a normal gait.

In addition to recognition of activities performed by a patient wearing the IKAFO 10, gait events (or particular phases of the gait cycle) may be similarly determined by analysis of the sensor data. Referring to FIG. 15A, joint angles, foot contacts (rear and front), and torque of the lower frame 120 are shown for a normal gait during four gait cycles. The following gait cycle transitions or events are apparent.

Foot flat to heel off: Pressures sensors at the rear of the foot are not pressed, the knee joint is at generally fully extended, and dorsiflexion of the ankle increases.

Heel off to Swing: Foot contact sensors at both the front and rear of the foot indicate no contact after toe off, foot rotation transitions from positive to negative, knee joint angular velocity (apparent from the slope of the knee angle curve) increases and the ankle continues a plantar flexion trajectory.

Swing to Heel strike: Foot contact sensors at the rear of the foot are not pressed, the knee joint is at full extension while ankle joint is almost at neutral position, and angular velocity of the shank (lower frame 120) features negative peaks at relative high frequencies.

Heel strike to Foot flat: Foot contact sensors at both front and rear parts of the foot indicate contact, ankle dorsiflexion increases, and, during complete stance, foot velocity is approximately zero.

It can therefore be recognized that important gait cycle transitions or events are recognizable by analysis of various sensor data and that each of the above gait cycle transitions or events may be associated with distinct features of more than a single sensor or sensor type.

Figure 15B:
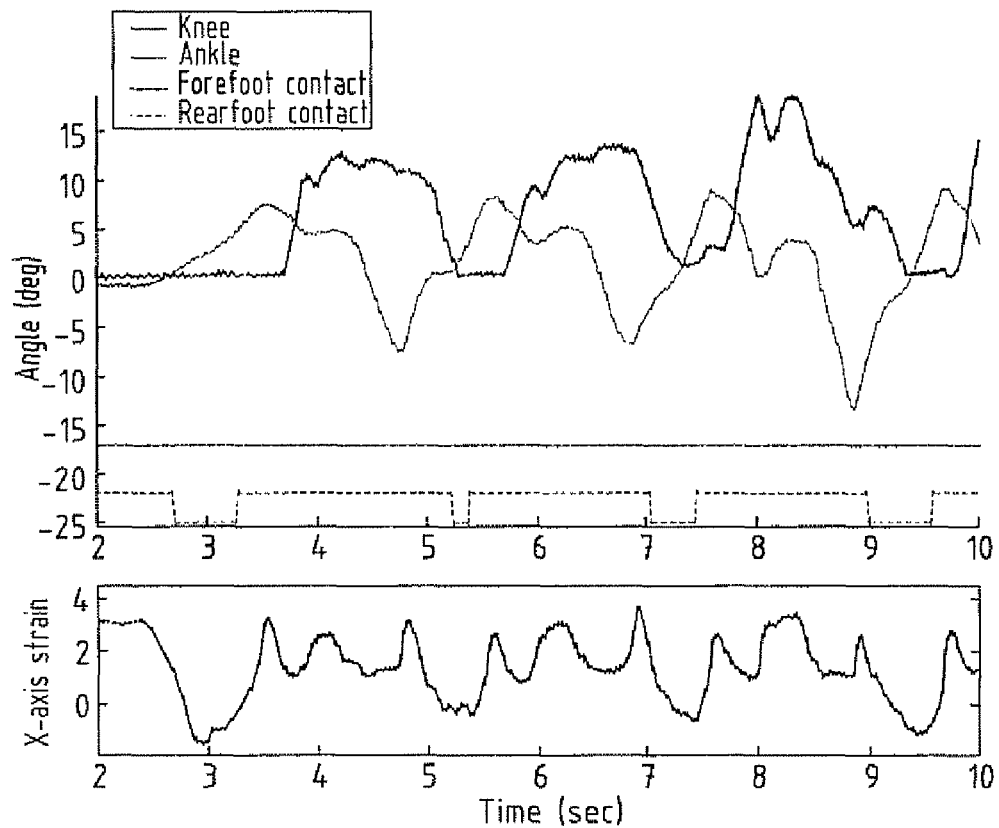
FIG. 15B is a graph depicting measured sensor data during a walking activity, showing data for four walking gait cycles according to a simulated abnormal or pathological, and gait.

While FIG. 15A shows sensor data measured during a normal gait, a patient wearing the IKAFO often will have some form of gait abnormality. Accordingly, recognition of gait cycle transitions or events according to more than a single criterion is important FIG. 15B shows data collected by a subject simulating an abnormal gait of a pathological situation by walking with the forefoot continuously in contact with the ground as if being unable to raise the foot for initial swing.

A logical consequence of the simulated abnormal gait is the altered shape of the swing phase angles of both the knee and ankle. Contact information of the heel is shifted remarkably, and forefoot contact information is not reliable during nearly the entire task. Use of redundant information from the various, different sensors helps to confirm gait cycle transitions and events despite potential deviations of any single measurement from a normal or ideal gait.

Based on observed correlations between activity transitions, as well as various activity or gait phases, rules can be defined for recognition of the activities and activity or gait phases. These rules may be implemented in the control program of the ambulatory unit to provide real-time evaluation of the sensor data and recognition of activities and activity or gait phases, in support of the control program in generation of control signals for actuators of the IKAFO.

Additionally, such rules may be implemented in a diagnostic program that is executed in the base unit, to provide information regarding a patient's usage of the IKAFO. The diagnostic program may provide a detailed usage profile, as well as analysis of the patient's measured gait, which is useful for fitting or adjusting the IKAFO to a patient's needs as well as determining therapeutic progress or success in the patient's treatment.

An example rule set is described, based on sensor data according to Table 1 below. As noted above, certain mechanical and kinematic aspects of the orthotic frame may be measured by more that a single sensor or sensor type, and therefore multiple different rules may be devised for each activity and activity or gait phase. Also, as noted above, variations or abnormalities of a patients individual gait pattern may result in modification to rules expressed, or in entirely different rules than those described herein. Accordingly, the rule set described herein is an example only, and is not intended as an expression of all possible or all desirable rules that may be implemented by the control program or the diagnostic program.

The rules described are based generally on instantaneous information in comparison with signal thresholds, identified in Table 2 for the sensor data set of Table 1. The signal threshold values may be derived from observational analysis of measured mechanical and kinematic sensor data.

TABLE 1

| | |
|---|---|
| fcs_fore | Foot contact sensor (forefoot) |
| fcs_rear | Foot contact sensor (heel) |
| KA | Knee Angle |
| KV | Knee Angular Velocity. |
| Kv_sign | Sign ('+' = 1 or '−' = 0) of knee angular velocity. |
| AA | Ankle Angle. |
| AV | Ankle angular Velocity. |
| d1 | Torsional deformation of the side bar of the lower frame 120 (X axis) |
| Ddef | d1 derivative |

TABLE 2

| | |
|---|---|
| thr_ka | Threshold for knee angle signal. |
| thr_ka2 | Second threshold for knee angle signal. |
| thr_aa | Threshold for ankle angle signal. |
| thr_aa_m | 'Medium' Threshold for ankle angle signal. |
| thr_aa_l | 'Low' Threshold for ankle angle signal. |
| thr_kv | Threshold for knee angular velocity. |
| thr_av | Threshold for ankle angular velocity. |
| thr_fcs_rear | Threshold for foot contact sensors. A value below the threshold indicates floor contact. |
| thr_fcs_fore | |
| thr_d | Threshold for structure deformation signal. |
| thr_ddef | Threshold for differential of structure deformation signal. |

Rules for detecting transition between standing stable and walking, and between walking and standing stable, are shown in Tables 3 and 4, respectively. Data samples are indicated for a given sample interval (k) or a previous sample interval (k−1). Signal redundancies are indicated by consecutive table rows that are not separated by "&", wherein multiple sensors provide the same or similar information. The first column indicates the sampled signal, while the second column indicates the associated sensor.

TABLE 3

| | |
|---|---|
| fce_rear(k − 1) < thr_fce_rear & fcs_rear (k) > thr_fcs_rear | Rear foot contact sensor |
| abs(d(k)) < thr_d & abs(AA(k)) > thr_aa | Strain gauges |
| KA(k) > thr_ka2 | Knee angle sensor |

TABLE 4

| | |
|---|---|
| (KA(k) < thr_ka2) & | Knee angle sensor |
| abs(AV(k)) < thr_av & | Ankle angle sensor |
| abs(AA(k)) < thr_aa & | Ankle angle sensor |
| abs(ddef(k)) < thr_ddef | strain gauges |

Figure 16A:
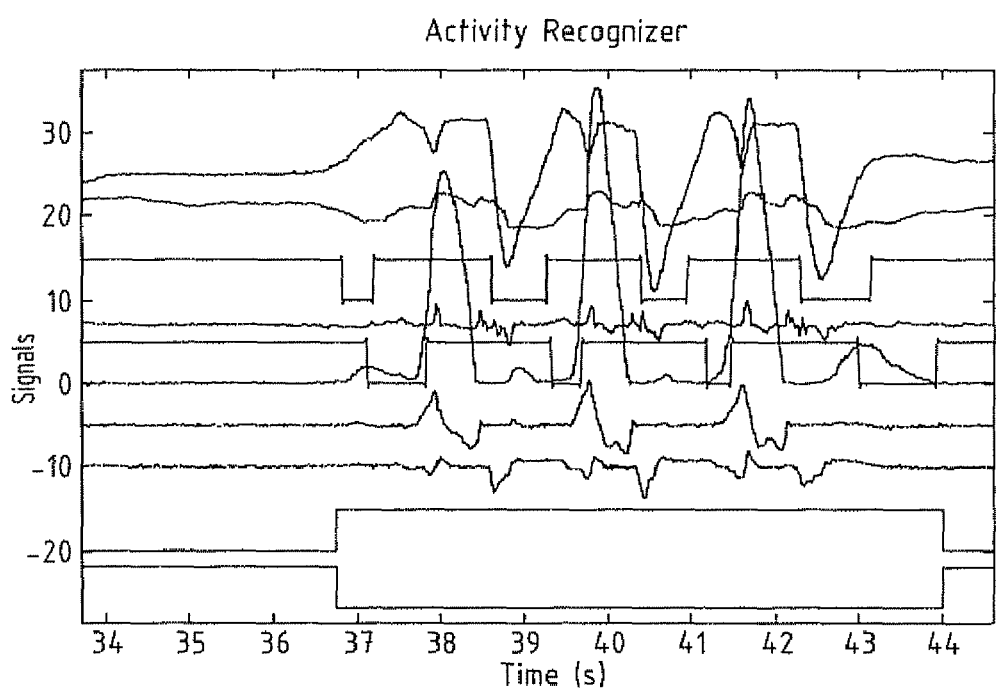
FIG. 16A is a graph depicting measured sensor data during a walking activity and a calculated activity recognition result based on a recognition rule applied to the measured data, in a normal walking gait.

Thresholds are derived to obtain detection referenced to contact information from the foot contact switches and supported by redundancy introduced with kinematics and supported forces of the orthotic frame. Extracted parameters such as differential of measured strain and angular velocity calculated by derivation of joint angular information are used in the illustrated rule. Also, alternative sensors may be employed such as inertial measurement units 860 may provide knee or ankle angle or angular velocity information in addition to, or instead of, the knee and ankle angle sensors. A high reliability of detection can be concluded from the results after a proper tuning procedure of the state machine parameters, as illustrated in FIG. 16A.

In order to discriminate between stance and swing phases during normal walking, rules such as those described in Tables 5-8 are be defined. Gait initiation recognition is assumed, and the definition of an initial state is required to differentiate between standing stable conditions and starting walking (a brief start state). Table 5 illustrates a rule for detecting the transition from start to stance.

TABLE 5

| | |
|---|---|
| fcs_rear(k) < thr_fcs_rear | Rear foot sensor |
| fcs_fore(k) < thr_fcs_fore | Forward foot sensor |
| & | |
| KA(k) < thr_ka | Knee angle sensor |

Table 6 summarizes a rule to detect the transition between stance and swing phases of a normal gait.

TABLE 6

| | |
|---|---|
| fcs_fore(k) > thr_fcs_fore | Forward foot contact sensor |
| abs(KV(k)) > thr_kv | Knee angular velocity |
| AA(k) > thr_aa & | Knee angle sensor, |
| KA(k) < thr_ka & | Ankle angle sensor |
| abs(AV(k)) < thr_av | |
| & | |
| fcs_rear(k) > thr_fcs_rear | Rear foot contact sensor |
| & | |
| fcs_rear(k − 1) < thr_fcs_rear | Rear foot contact sensor |

As discusses above, while evaluation of a normal walking gait provides a useful baseline for analysis and for generation of rules for detecting gait activities and events, pathological conditions resulting in an abnormal gait must be considered Table 7 illustrates another rule for detecting transition between stance and swing phases, but in a simulated drop foot gait.

TABLE 7

| | |
|---|---|
| fcs_fore(k) > thr_fcs_fore | Forward foot contact sensor |
| abs(KV(k)) > thr_kv | Knee angle sensor |
| AA(k) > thr_aa & | Knee angle sensor, |
| KA(k) < thr_kv & | Ankle angle sensor |
| abs(AV(k)) < thr_av | |
| & | |
| fcs_rear(k − 1) < thr_fcs_rear & | Rear foot contact sensor, |
| KV(k) > thr_kv | Knee angle sensor |
| fcs_rear(k) > thr_fcs_rear | Rear foot contact sensor |

Table 8 shows another rule for a simulated drop foot gait, this time for detecting transition from swing to stance.

TABLE 8

| | |
|---|---|
| fcs_rear(k) < thr_fsr_rear | Rear foot contact sensor |
| kv_sign == 0 (−) | Knee angle sensor |
| & | |
| KA(k) < thr_ka | Knee angle sensor |
| & | |
| KV(k) < thr_kv | Knee angle sensor |
| & | |
| fcs_fore(k) > thr_fsr_fore | Forward foot contact sensor |

Figure 16B:
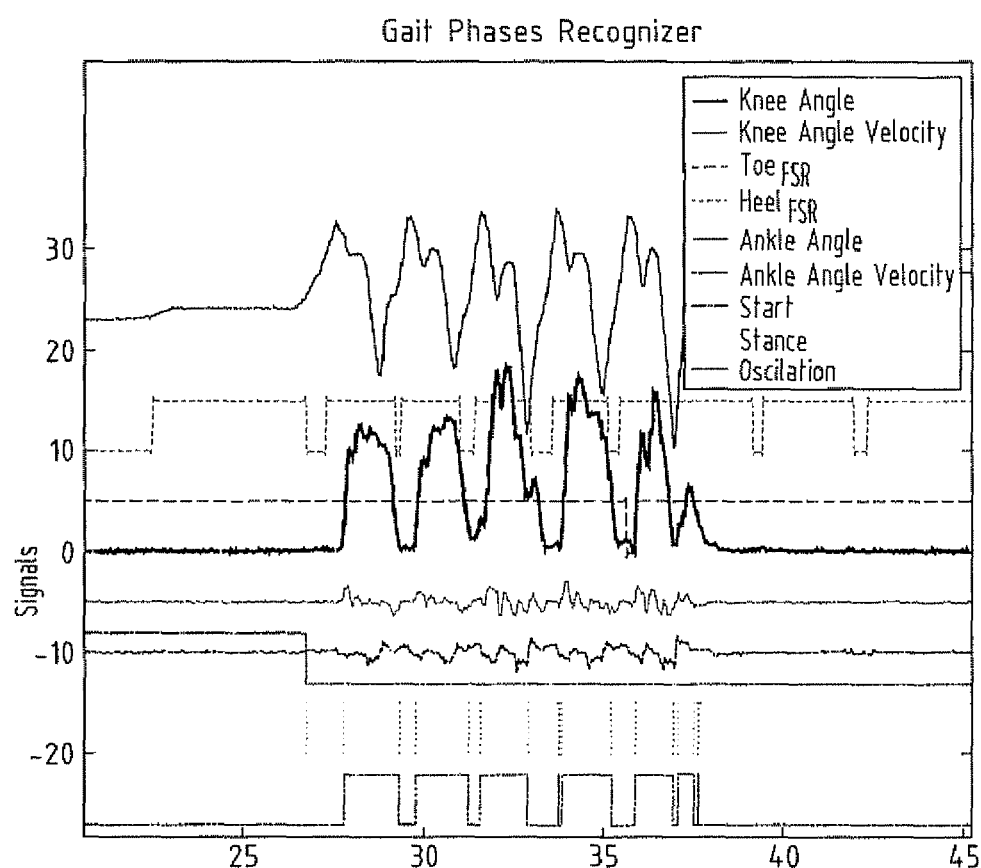
FIG. 16B is a graph depicting measured sensor data during a walking activity and a calculated activity recognition result based on a recognition rule applied to the measured data, in a simulated abnormal (pathological) walking gait.

Because information extracted from foot contact sensors may be unreliable during a pathological gait situation, a higher level of redundancy may be introduced to ensure a proper detection of swing and stance phases. FIG. 16B shows a result of recognition of stance and swing phases, with a high reliability, during simulated pathological gait case. The reliability of the rules is improved in such an abnormal gait by defining rules that are more independent from the foot contact sensor information that may be lost or unreliable.

For certain transitions, it is useful to consider a single transition as a sequence of partial transition events. For example, Tables 9-11 show rules for detecting a transition from sitting down to standing stable, wherein the transition is considered in three phases Table 9 illustrates a rule for detecting a sitting to a start standing activity, while table 10 illustrates a rule for detecting a start standing to a standing up activity, and table 11 illustrates a rule for detecting a standing up to a standing stable activity. Thus, the transition from sitting down to standing stable may be viewed as a sequence of activities transitioning from sitting to starting to stand, to standing up and finally to standing stable.

TABLE 9

| | |
|---|---|
| d1(k) > um_d1 | Strain gauge |
| & | |
| fcs_rear(k) > fcs_rear | Rear foot contact sensor |
| & | |
| abs(KV(k)) < um_kv | Knee angle sensor |
| & | |
| KA(k) > um_ka | Knee angle sensor |

TABLE 10

| | |
|---|---|
| AA(k) > um_aa | Ankle angle sensor |
| & | |
| KA(k) < um_ka | Ankle angle sensor |
| & | |
| fcs_rear(k) < fcs_rear | Rear foot contact sensor |
| KA(k) < um_ka | Knee angle sensor |

TABLE 11

| | |
|---|---|
| d1(k) < um_d1 | Strain gauge |
| & | |
| KA(k) > um_ka | Knee angle sensor |

Starting from a static seated condition (sitting down), a loading phase is detected, which indicates the subject's intention to get up, shortly before kinematics detect the initiation of the procedure. The transition ends with the subject standing stable.

Similarly, the transition from standing stable to sitting down may be considered in a first transition from standing stable to seating (beginning to sit down) and a second transition from seating to the final state of sitting down. Tables 12 and 13 illustrate rules for the transitions from standing stable to seating, and from seating to sitting down, respectively.

TABLE 12

| | |
|---|---|
| (d1(k) > um_d1) & | Strain gauge, |
| ((abs(KV(k)) > um_kv) | Knee angle sensor |
| abs(KV(k)) < um_kv | Knee angle sensor |
| & | |
| KA(k) > um_ka | Knee angle sensor |

TABLE 13

| | |
|---|---|
| AA(k) > um_ka | Ankle angle sensor |
| & | |
| KA(k) < um_ka | Knee angle sensor |

Starting from a static condition while standing stable, the seating procedure is detected based upon cinematic information as can be seen from the rule described in tables 12 and 13. In this case, bar loading data does not provide much information to detect the subject information. The transition ends with the subject sitting down.

A rule for detecting an activity of climbing stairs (transitioning from stable standing to going up stairs) is shown in Table 14. The activity is begun from a stable standing state, and the subject initiates the activity with the non-orthotic leg.

TABLE 14

| | |
|---|---|
| d1(k) > um_d1 | Strain gauge |
| & | |
| AA(k) < um_a | Ankle angle sensor |
| & | |
| fcs_rear(k) == 0 | Rear foot contact sensor |

Foot contact sensors considered together with strain gauges and ankle kinematics provided an efficient and reliable determination of this activity. Table 15 illustrates a rule for detecting transition from climbing stairs back to stable standing.

TABLE 15

| | |
|---|---|
| d1(k) > um_d1_min | Strain gauge |
| d1(k) < um_d1_max | Strain gauge |
| & | |
| (AA(k) < um_a_min) & | Ankle angle sensor |
| ((AA(k) > um_a_max) | |

With the knee joint locked throughout the stair climbing activity, detection based on ankle kinematics is confirmed by load stabilization according to the strain gauge.

Rules for detecting a downslope walking activity are described in Tables 16 and 17, wherein the transition from standing stable to downslope walking is considered in a first transition from standing stable to beginning downslope, and a second transition from beginning downslope to walking downslope.

TABLE 16

| | |
|---|---|
| d1(k) < um_d1_min | Strain gauge |
| & | |
| abs(AV(k)) < um_av | Ankle angle sensor |
| & | |
| AA(k) < um_a_min | Ankle angle sensor |

TABLE 17

| | |
|---|---|
| (AV(k) > um_av) & | Ankle angle sensor |
| (AA(k) > um_a_dors) | |
| d1(k) < um_d1 | Ankle angle sensor |

The subject begins the transition with the non-orthotic leg, and the orthotic knee joint remains locked during the course of downslope walking. Heel strike may be significantly delayed during downslope walking (or during the transition from stable standing to downslope walking) and so ankle angular information is employed for detection. Also, the strain gauge signal decreases, since weight is shifted to the non-orthotic leg, and therefore becomes useful to differentiate between this transition and the transition from stable standing to level walking (the start walking activity).

Similarly, a rule for detection of the termination of downslope walking (transitioning from downslope walking to standing stable) employs information from the strain gauge and the ankle angle, as seen in Table 18.

TABLE 18

| (d1(k) > um_d1_min) & (d1(k) < um_d1_max) | Strain gauge |
|---|---|
| & | |
| (AA(k) > um_a_min) & (AA(k) < um_a_max) | Ankle angle sensor |

Thus, analysis of the sensor data collected by the ambulatory unit 900 may be analyzed, either by the control program of the ambulatory unit 900 or by the diagnostic program of the base unit.

In the ambulatory unit 900, information about the ambulatory activities, activity transitions, and activity or gait phases may be used to control actuators of the orthotic frame 100 to affect active assistive strategies to assist a patient's gait. For example, activation of the knee actuator 300 to select the stiff mode or the flexible mode may be synchronized to detection of certain gait events.

Also, knowledge of an activity being performed by a patient may be used to alter such a control function from a baseline. In the event of upslope or downslope walking, timing between a given gait event and actuation of the knee actuator 300 may be affected for optimal assistance to the patient.

Accordingly, while activation of the knee actuator 300 may be triggered by detection of a gait event, knowledge of the ambulatory activity that the patient is performing allows selection of a gait event most appropriate for the activity, as well as introduction or modification of a time delay factor between detection of the gait event and actuation of the knee actuator 300, or even modification of threshold levels used for gait event detection during the course of a given activity.

It will be understood that the above-described embodiments of the invention are illustrative in nature, and that modifications thereof may occur to those skilled in the art. Accordingly, this invention is not to be regarded as limited to the embodiments disclosed herein, but is to be limited only as defined in the appended claims.

The invention claimed is:

1. An actuator having a variable compressive stiffness for placement on an orthosis having a joint portion and arranged for biomechanical functional compensation of ambulatory disorders, comprising:
   a first cylinder;
   a second cylinder slidably disposed at least partially within the first cylinder and biased toward an extended position by a first biasing member;
   a shaft slidably disposed at least partially within the second cylinder and biased toward an extended position by a second biasing member; and
   a locking mechanism movable between a locked position providing a first resistance wherein the first and second cylinders are locked together in a fixed position, and an unlocked position providing a second resistance wherein the first and second cylinders are movable relative to one another;
   wherein the actuator is placed at a joint portion located on the orthosis.

2. The actuator according to claim 1, wherein the second biasing member provides a different biasing force than the first biasing member.

3. The actuator according to claim 1, wherein the first and second biasing members are comprised of a first and a second spring, respectively, and the second spring has a different stiffness than the first spring.

4. The actuator according to claim 1, wherein the locking mechanism is biased toward the locked position.

5. An orthosis for biomechanical evaluation and functional compensation of ambulatory disorders, comprising:
   an orthotic frame having a proximal frame, a distal frame, a foot support, a knee joint coupling a distal end of the proximal frame to a proximal end of the distal frame;
   a knee actuator disposed on the orthotic frame and configured to control flexion of the knee joint according to a variable resistance;
   a selector having at least a first position wherein the knee actuator provides a first resistance and a second position wherein the knee actuator provides a second resistance; and
   a control element connected to the selector and configured to move the selector between the first and second position according to at least one aspect of an ambulatory or related activity.

6. The orthosis according to claim 5, wherein the knee actuator comprises a first biasing member for providing the first resistance and a second biasing member for providing the second resistance.

7. The orthosis according to claim 6, wherein the first biasing member is a first spring having a first stiffness.

8. The orthosis according to claim 6, wherein the second biasing member is a second spring having a second stiffness.

9. The orthosis according to claim 5, wherein the knee actuator comprises:
   a first cylinder;
   a second cylinder slidably disposed at least partially within the first cylinder and biased toward an extended position by a first biasing member; and
   a shaft slidably disposed at least partially within the second cylinder and biased toward an extended position by a second biasing member.

10. The orthosis according to claim 9, further comprising a locking mechanism configured and arranged to selectively lock the first and second cylinders together in a fixed position.

11. The orthosis according to claim 9, wherein the second biasing member provides a greater biasing force than the first biasing member.

12. The orthosis according to claim 9, wherein the first and second biasing members are comprised of first and second springs, respectively, the second spring having a greater stiffness than the first spring.

13. The orthosis according to claim 5, wherein the knee joint has a variable instantaneous axis of rotation mimicking an instantaneous helical axis of a human knee.

14. The orthosis according to claim 5, wherein the control element comprises a mechanical coupling connected between an ankle joint connected to the distal end of the distal frame, and the selector, the mechanical coupling being configured to move the selector between the first and second positions according to an angle of flexion of the ankle joint.

15. The orthosis according to claim 14, wherein the control element is a cable movable according to an angle of the ankle, the cable operating the selector to unlock the knee actuator.

16. An orthosis for biomechanical evaluation and functional compensation of ambulatory disorders, comprising:

an orthotic frame having a proximal frame adapted for fitting to a user's upper leg, a distal frame adapted for fitting to the user's lower leg, a foot support, a knee joint coupling a distal end of said proximal frame to a proximal end of said distal frame, and an ankle joint coupling a distal end of said distal frame to said foot support;

a knee actuator disposed on the orthotic frame and configured to control flexion of the knee joint according to a variable resistance;

an ankle actuator coupled between said distal frame and said foot support providing a dorsal bias to position said foot support against dorsal flexion and a plantar bias to position said foot support against plantar flexion, whereby the ankle actuator controls flexion of said ankle joint; and a control element connected to the knee actuator and at least one of the ankle joint and foot support, the control element movable according to an angle of one of the ankle joint and the foot support, the control element arranged to activate the knee actuator when the ankle joint or the foot support reaches a predetermined degree of flexion.

17. The orthosis according to claim 16, wherein the control element is a cable movable according to an angle of the ankle, the cable operating the selector to unlock the knee actuator.

18. The orthosis according to claim 16, wherein said knee actuator comprises:

a first cylinder;

a second cylinder slidably disposed at least partially within said first cylinder and biased toward an extended position by a first biasing member; and a shaft slidably disposed at least partially within said second cylinder and biased toward an extended position by a second biasing member.

19. The orthosis according to claim 18, further comprising a locking mechanism configured and arranged to selectively lock said first and second cylinders together in a fixed position.

20. The orthosis according to claim 18, wherein said second biasing member provides a greater biasing force than said first biasing member.

* * * * *